(12) United States Patent
Fadhel et al.

(10) Patent No.: US 11,666,225 B2
(45) Date of Patent: Jun. 6, 2023

(54) METHOD AND SYSTEM FOR FLUENCE MATCHING IN PHOTOACOUSTIC IMAGING

(71) Applicants: Muhannad N. Fadhel, Richmond Hill (CA); Michael C. Kolios, Hamilton (CA)

(72) Inventors: Muhannad N. Fadhel, Richmond Hill (CA); Michael C. Kolios, Hamilton (CA)

(*) Notice: Subject to any disclaimer, the term of this patent is extended or adjusted under 35 U.S.C. 154(b) by 344 days.

(21) Appl. No.: 16/958,995

(22) PCT Filed: Jan. 25, 2019

(86) PCT No.: PCT/CA2019/050088
§ 371 (c)(1),
(2) Date: Jun. 29, 2020

(87) PCT Pub. No.: WO2019/144232
PCT Pub. Date: Aug. 1, 2019

(65) Prior Publication Data
US 2020/0329974 A1    Oct. 22, 2020

Related U.S. Application Data

(60) Provisional application No. 62/621,942, filed on Jan. 25, 2018.

(51) Int. Cl.
*A61B 5/00* (2006.01)
*A61B 5/1455* (2006.01)

(52) U.S. Cl.
CPC ........ *A61B 5/0095* (2013.01); *A61B 5/14552* (2013.01); *A61B 5/7203* (2013.01); *A61B 5/725* (2013.01)

(58) Field of Classification Search
CPC . A61B 5/0095; A61B 5/14552; A61B 5/7203; A61B 5/725; A61B 5/14551; G01N 29/2418
See application file for complete search history.

(56) References Cited

U.S. PATENT DOCUMENTS 9,271,654 B2    3/2016   Razansky et al.
9,456,805 B2    10/2016  Zalev et al.
(Continued)

FOREIGN PATENT DOCUMENTS

EP          3056137 A1      8/2016
WO    WO-2013188709 A1 *  12/2013   ........... A61B 5/0035

OTHER PUBLICATIONS

Wang et al., "Single-cell label-free photoacoustic flowoxigraphy in vivo," Proc. Natl. Acad. Sci. U. S. A., 2013, 110(15): 5759-5764.
(Continued)

*Primary Examiner* — Christopher Koharski
*Assistant Examiner* — Taylor Deutsch
(74) *Attorney, Agent, or Firm* — Tony R. Orsi; Bereskin & Parr LLP/S.E.N.C.R.L., s.r.l.

(57) ABSTRACT

Various embodiments are described herein for an imaging device and associated method for performing fluence compensation on a photoacoustic (PA) image of at least a portion of an object for sets of RF acoustic response signals that are obtained using different illumination wavelengths. A first set of RF acoustic response signals is fluence matched to a second set of RF acoustic response signals by determining relative frequency data for first set of RF acoustic response signals relative to the second set of RF acoustic response signals and using the relative frequency data to filter the first set of RF acoustic response signals.

28 Claims, 16 Drawing Sheets

(56) References Cited

U.S. PATENT DOCUMENTS

| | | | |
|---|---|---|---|
| 9,551,789 | B2 | 1/2017 | Morscher et al. |
| 9,572,497 | B2 | 2/2017 | Razansky et al. |
| 9,724,072 | B2 | 8/2017 | Herzog et al. |
| 11,287,309 | B2 * | 3/2022 | Schmid .................. G01H 1/003 |
| 2013/0276542 | A1 * | 10/2013 | Herzog ..................... G01J 1/04 |
| | | | 73/655 |
| 2015/0075287 | A1 | 3/2015 | Herzog et al. |
| 2016/0235304 | A1 | 8/2016 | Tzoumas et al. |
| 2017/0042428 | A1 | 2/2017 | Kellnberger et al. |
| 2017/0069089 | A1 | 3/2017 | Zalev |
| 2017/0100040 | A1 | 4/2017 | Zalev et al. |

OTHER PUBLICATIONS

Sivaramakrishnan et al., "Limitations of quantitative photoacoustic measurements of blood oxygenation in small vessels," Phys. Med. Biol., 2007, 52(5): 1349-1361.

Manohar et al., "Photoacoustics: a historical review," Adv. Opt. Photonics, 2016, 8(4): 586-617.

Paproski et al., "Multi-wavelength photoacoustic imaging of inducible tyrosinase reporter gene expression in xenograft tumors," Sci. Rep., 2014, 4: 5329, pp. 1-7.

Zhang et al., "Effects of wavelength-dependent fluence attenuation on the noninvasive photoacoustic imaging of hemoglobin oxygen saturation in subcutaneous vasculature in vivo," Proc. SPIE 6856, Photons Plus Ultrasound: Imaging and Sensing 2008: The Ninth Conference on Biomedical Thermoacoustics, Optoacoustics, and Acousto-optics, 68561T-1 to -15.

May et al., "Photoacoustic Imaging of Cancer Treatment Response: Early Detection of Therapeutic Effect from Thermosensitive Liposomes," PloS One, 2016, 11(10): e0165345, pp. 1-21.

Ma et al., "Multispectral optoacoustic tomography (MSOT) scanner for whole-body small animal imaging," Opt. Express, 2009, 17(24): 21414-21426.

Cox et al., "Quantitative spectroscopic photoacoustic imaging: a review," J. Biomed. Opt., 2012, 17(6): 061202-1 to -22.

Jacques et al., "Optical properties of biological tissues: a review," Phys. Med. Biol., 2013, 58(11): R37-61; and "Corrigendum: Optical properties of biological tissues: a review", Phys. Med. Biol., 2013, 58(11): 5007-5007.

Jacques et al., "Tutorial on diffuse light transport," J. Biomed. Opt., 2008, 13(4): 041302-1 to -19.

Yuan et al., "Reconstruction of optical absorption coefficient maps of heterogeneous media by photoacoustic tomography coupled with diffusion equation based regularized Newton method," Opt. Express, 2007, 15(26): 18076-18081.

Yuan et al., "Quantitative photoacoustic tomography: Recovery of optical absorption coefficient maps of heterogeneous media," Appl. Phys. Lett., 2006, 88(23): 231101-1 to -3.

Bu et al., "Model-based reconstruction integrated with fluence compensation for photoacoustic tomography," IEEE Trans. Biomed. Eng., 2012, 59(5): 1354-1363.

Cox et al., "The challenges for quantitative photoacoustic imaging," Photons Plus Ultrasound: Imaging and Sensing 2009: The Tenth Conference on Biomedical Thermoacoustics, Optoacoustics, and Acousto-optics, Oraevsky et al., ed., Proc. of SPIE vol. 7177, paper 717713-1 to -9.

Laufer et al., "Quantitative determination of chromophore concentrations from 2D photoacoustic images using a nonlinear model-based inversion scheme," Appl. Opt., 2010, 49(8): 1219-1233.

Laufer et al., "Quantitative spatially resolved measurement of tissue chromophore concentrations using photoacoustic spectroscopy: application to the measurement of blood oxygenation and haemoglobin concentration," Phys. Med. Biol., 2007, 52(1): 141-168.

Cox et al., "Two-dimensional quantitative photoacoustic image reconstruction of absorption distributions in scattering media by use of a simple iterative method," Appl. Opt., 2006, 45(8): 1866-1875.

Zemp et al., "Quantitative photoacoustic tomography with multiple optical sources," Appl. Opt., 2010, 49(18): 3566-3572 (web copy: 16 pages).

Pulkkinen et al., "Direct Estimation of Optical Parameters from Photoacoustic Time Series in Quantitative Photoacoustic Tomography," IEEE Trans. Med. Imaging, 2016, 35(11): 2497-2508.

Fonseca et al., "Three-dimensional photoacoustic imaging and inversion for accurate quantification of chromophore distributions," Proc. of SPIE, 2017, 10064: 1006415-1 to -9.

Brochu et al., "Towards Quantitative Evaluation of Tissue Absorption Coefficients Using Light Fluence Correction in Optoacoustic Tomography," IEEE Trans. Med. Imaging, 2017 (epub 2016), 36(1): 322-331.

Rajian et al., "Quantitative photoacoustic measurement of tissue optical absorption spectrum aided by an optical contrast agent," Opt. Express, 2009, 17(6): 4879-4889.

Daoudi et al., "Correcting photoacoustic signals for fluence variations using acousto-optic modulation," Opt. Express, 2012, 20(13): 14117-14129.

Shao et al., "Consecutively reconstructing absorption and scattering distributions in turbid media with multiple-illumination photoacoustic tomography," J. Biomed. Opt., 2014, 19(12): 126009.

Ripoll et al., "Quantitative point source photoacoustic inversion formulas for scattering and absorbing media," Phys. Rev. E Stat. Nonlin Soft Matter Phys., 2005, 71(3 Pt 1): 031912-1 to -9.

Yin et al., "Tomographic imaging of absolute optical absorption coefficient in turbid media using combined photoacoustic and diffusing light measurements," Opt. Lett., 2007, 32(17): 2556-2558.

Tzoumas et al., "Eigenspectra optoacoustic tomography achieves quantitative blood oxygenation imaging deep in tissues," Nat. Commun., 2016, 7: 12121, pp. 1-10.

Kirchner et al., "Local context encoding enables machine learning-based quantitative photoacoustics," ArXiv170603595 Phys., 2017, pp. 1-24.

Tzoumas et al., "Unmixing Molecular Agents From Absorbing Tissue in Multispectral Optoacoustic Tomography," IEEE Trans. Med. Imaging, 2014, 33(1): 48-60.

Tzoumas et al., "Effects of multispectral excitation on the sensitivity of molecular optoacoustic imaging," J. Biophotonics, 2015, 8(8): 629-637.

Razansky et al., "Multispectral opto-acoustic tomography of deep-seated fluorescent proteins in vivo," Nat. Photonics, 2009, 3(7): 412-417.

Glatz et al., "Blind source unmixing in multi-spectral optoacoustic tomography," Opt. Express, 2011, 19(4): 3175-3184.

Kim et al., "In vivo three-dimensional spectroscopic photoacoustic imaging for monitoring nanoparticle delivery," Biomed. Opt. Express, 2011, 2(9): 2540-2550.

Hysi et al., "Probing the in vivo changes in oxygen saturation with photoacoustic imaging as a non-invasive means of assessing treatment progression," Photons Plus Ultrasound: Imaging and Sensing 2015, Oraevsky et al., ed., Proc. of SPIE, 9323: 93231Z-1 to -8.

Bigelow et al., "Estimation of total attenuation and scatterer size from backscattered ultrasound waveforms," J. Acoust. Soc. Am., 2005, 117(3 Pt 1): 1431-1439.

Bigelow et al., "In vivo ultrasonic attenuation slope estimates for detecting cervical ripening in rats: Preliminary results," J. Acoust. Soc. Am., 2008, 123(3): 1794-1800 (manuscript copy: 16 pages).

Wang, "Tutorial on Photoacoustic Microscopy and Computed Tomography," IEEE J. Sel. Top. Quantum Electron., 2008, 14(1): 171-179.

Xu et al., "Photoacoustic imaging in biomedicine," Rev. Sci. Instrum., 2006, 77(4): 041101.

Xu et al., "Photoacoustic spectrum analysis for microstructure characterization in biological tissue: A feasibility study," Appl. Phys. Lett., 2012, 101(22): 221102-1 to -5.

Bosschaart et al., "A literature review and novel theoretical approach on the optical properties of whole blood," Lasers Med. Sci., 2014, 29(2): 453-479.

Naser et al., "Improved photoacoustic-based oxygen saturation estimation with SNR-regularized local fluence correction," IEEE Trans. Med. Imaging, 2019, 38(2): 561-571.

(56) References Cited

OTHER PUBLICATIONS

Diebold et al., "Photoacoustic monopole radiation in one, two, and three dimensions," Phys. Rev. Lett., 1991, 67(24): 3384-3387, and Figs. 1 and 2.

Yao et al., "Backscatter coefficient measurements using a reference phantom to extract depth-dependent instrumentation factors," Ultrason. Imaging, 1990, 12(1): 58-70.

Yang et al., "An Improved Median-based Otsu Image Thresholding Algorithm," AASRI Procedia, 2012, 3: 468-473.

Mallidi et al., "Multiwavelength Photoacoustic Imaging and Plasmon Resonance Coupling of Gold Nanoparticles for Selective Detection of Cancer," Nano Lett., 2009, 9(8): 2825-2831 (manuscript copy: 17 pages).

International Search Report and Written Opinion dated Apr. 26, 2019 in International Patent Application No. PCT/CA2019/050088 (12 pages).

Beard, "Biomedical photoacoustic imaging," Interface Focus, 2011, 1(4): 602-631.

Jiang et al., "Spatially varying optical and acoustic property reconstruction using finite-element-based photoacoustic tomography," J. Opt. Soc. Am. A, 2006, 23(4): 878-888 (web copy: 26 pages).

Paltauf et al., "Iterative reconstruction algorithm for optoacoustic imaging," The Journal of the Acoustical Society of America, 2002, 112(4): 1536-44.

Thera Medical GmbH, web pages, accessed Aug. 28, 2017 <http://www.ithera-medical.com> (5 pages).

Brillant et al., "Dynamic and accurate assessment of acetaminophen-induced hepatotxicity by integrated photoacoustic imaging and mechanistic biomarkers in vivo," Toxicology and Applied Pharmacology, 2017, 332: 64-74.

Joseph et al., "Evaluation of precision in optoacoustic tomography for preclinical imaging in living subjects," J Nucl Med., 2017, 58(5): 807-817.

Haedicke et al., "Sonophore labeled RGD: a targeted contrast agent for optoacoustic imaging," Photoacoustics, 2017, 6:1-8.

Berer, "Photoacoustics," Research Center for Non Destructive Testing GmbH (RECENDT), accessed on Sep. 7, 2017 <http://www.recendt.at/528_ENG_HTML.php> (2 pages).

"Photoacoustic imaging," Wikipedia, 2017 <https://en.wikipedia.org/wiki/Photoacoustic_imaging> (6 pages).

"Chromophore," Wikipedia, 2017 <https://en.wikipedia.org/wiki/Chromophore> (3 pages).

Larson et al., "Spectral Imaging with Linear Unmixing," Microscopy U, accessed on Sep. 7, 2017 <https://www.microscopyu.com/tutorials/spectral-imaging-with-linear-unmixing> (4 pages).

Dickinson et al., "Education in Microscopy and Digital Imaging," Carl Zeiss Microscopy Online Campus, access on Sep. 7, 2017 <http://zeiss-campus.magnet.fsu.edu/articles/spectralimaging/introduction.html> (15 pages).

Fadhel et al., "Ultrasound spectral analysis of photoacoustic signals from red blood cell populations at different optical wavelengths," Proc. of SPIE 10064, Photons Plus Ultrasound: Imaging and Sensing 2017, 1006417-1 to -8.

Merčep et al., "Combined Pulse-Echo Ultrasound and Multispectral Optoacoustic Tomography with a Multi-Segment Detector Array," IEEE Transactions on Medical Imaging, 2017, 36(10): 2129-2137.

Kirchner et al., "Context encoding enables machine learning based quantitative photoacoustics," ArXiv170603595 Phys., 2017, pp. 1-15.

\* cited by examiner

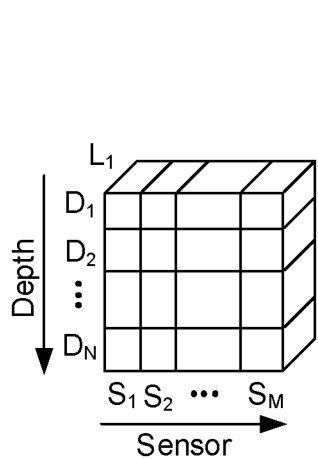
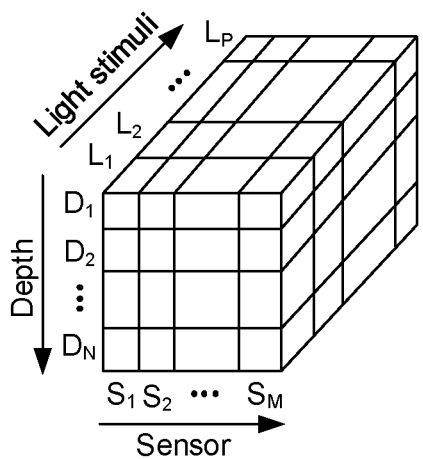
FIG. 3B  FIG. 3C
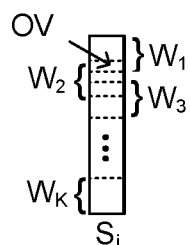
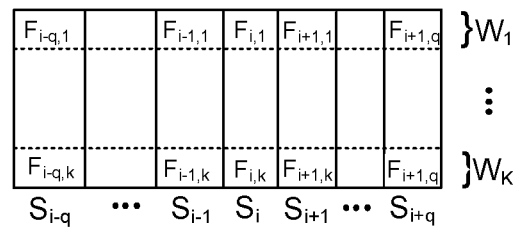
FIG. 3D  FIG. 3E
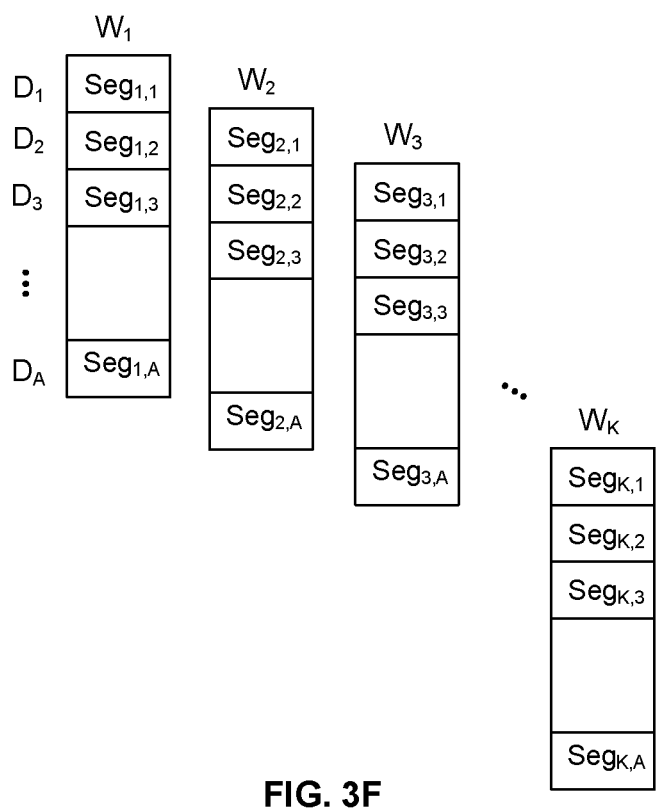
FIG. 3F

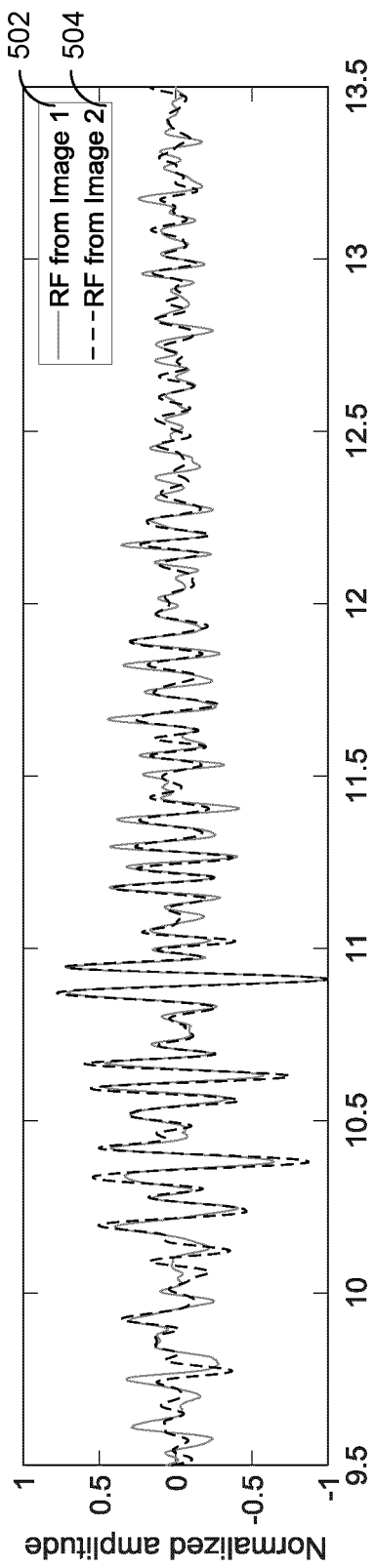
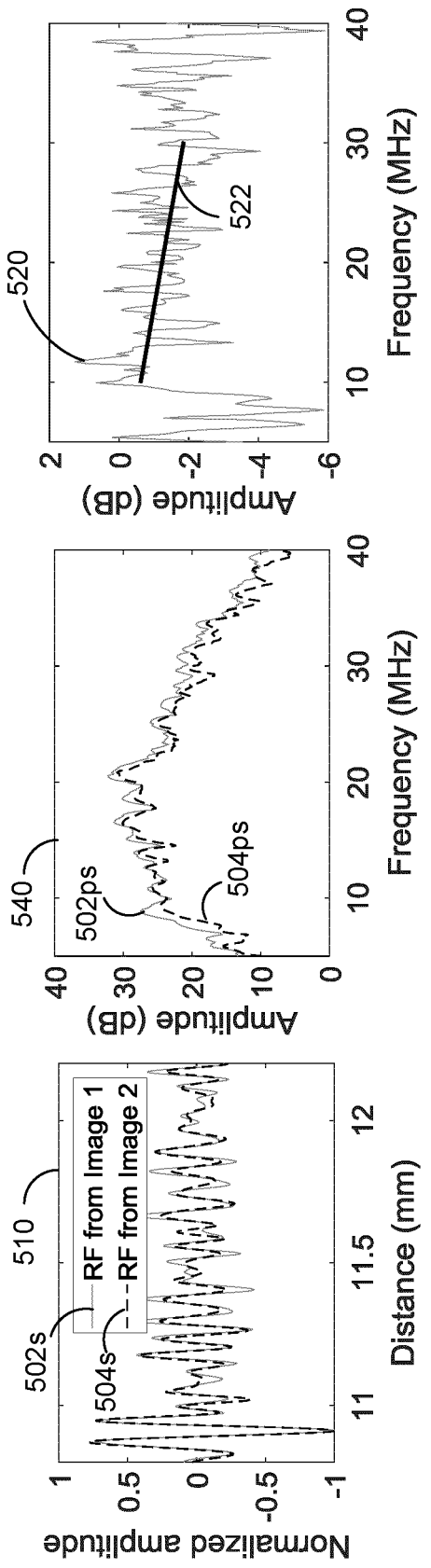

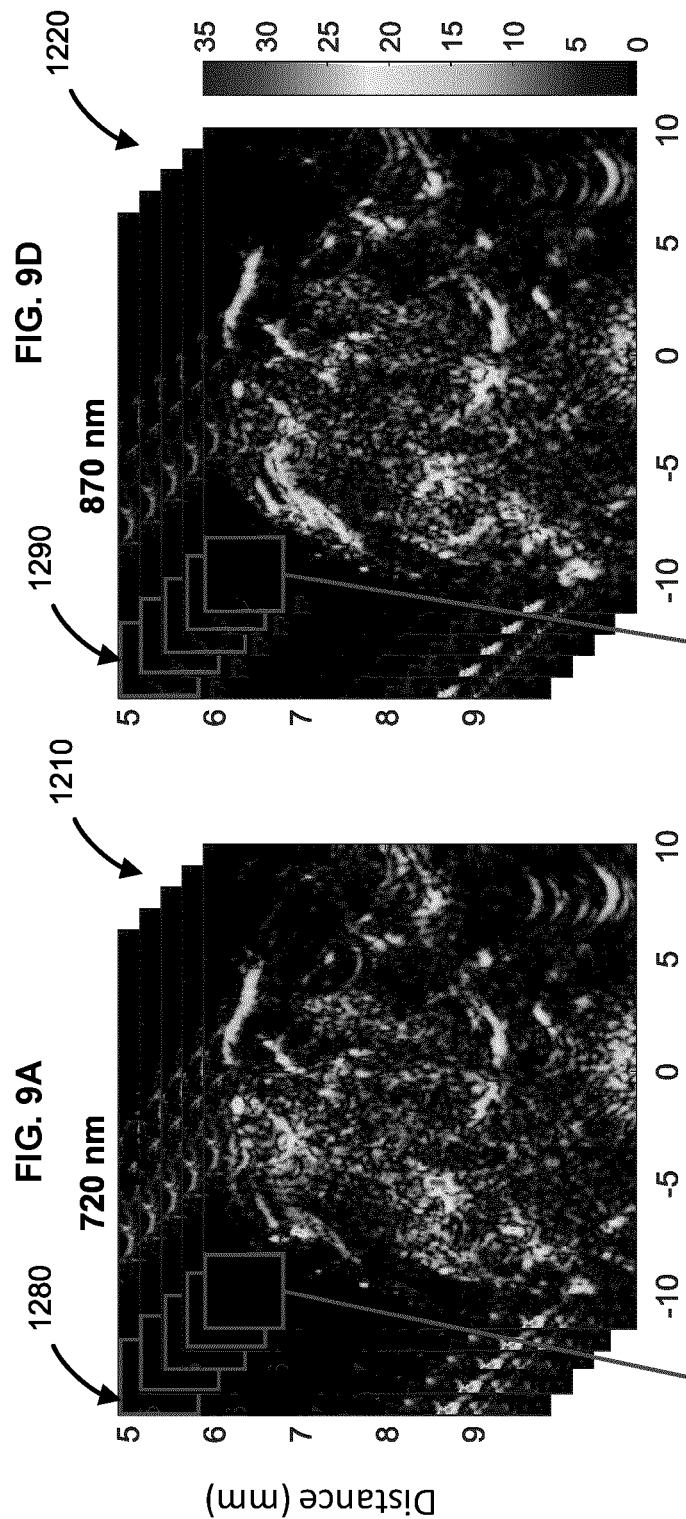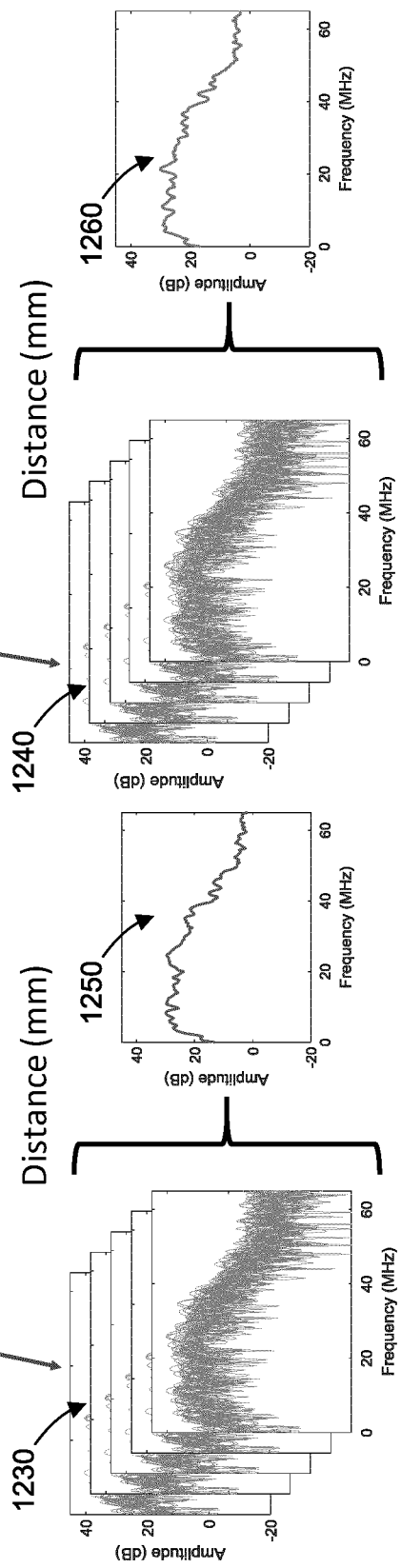

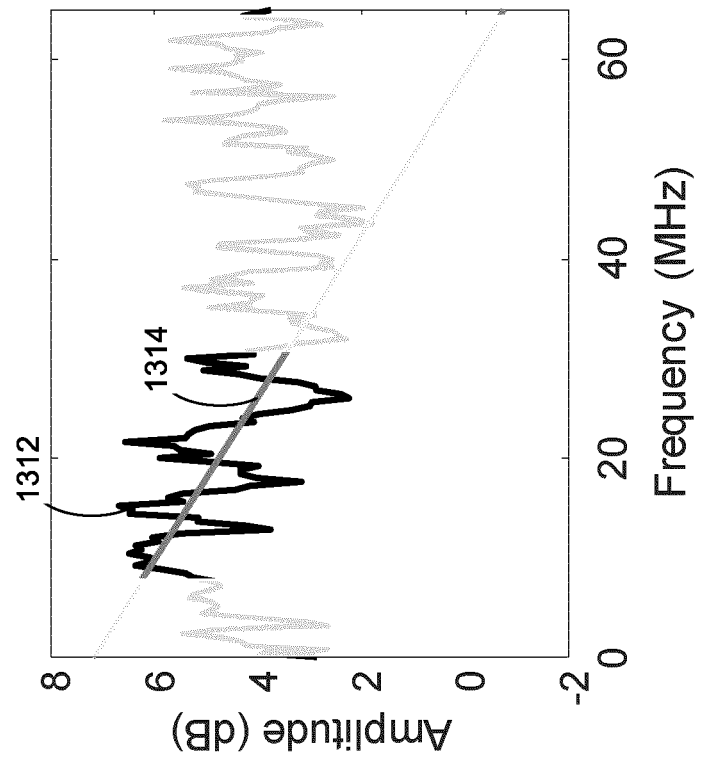
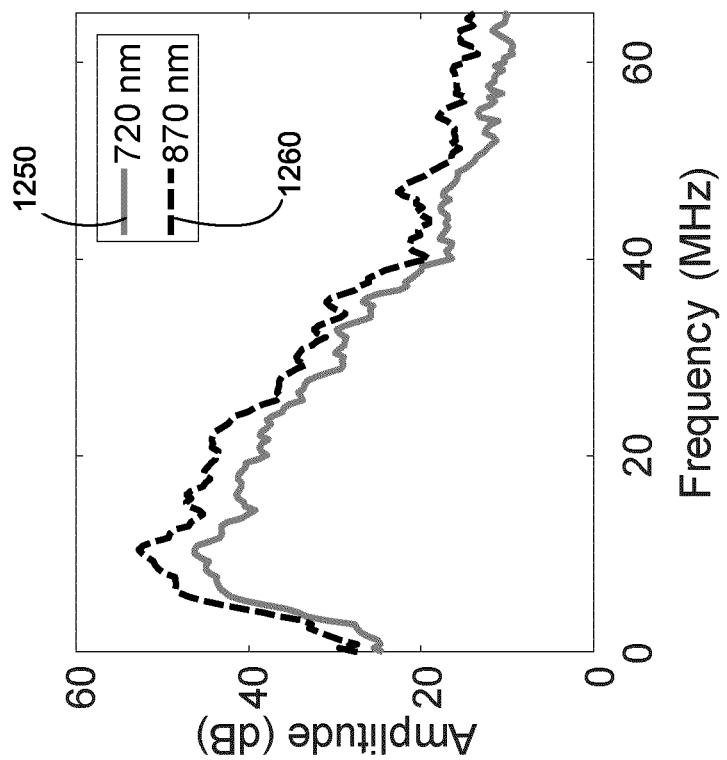
FIG. 10B
FIG. 10A

METHOD AND SYSTEM FOR FLUENCE MATCHING IN PHOTOACOUSTIC IMAGING

CROSS-REFERENCE TO RELATED APPLICATION

This application is a 35 USC § 371 national stage entry of International Patent Application No. PCT/CA2019/050088, filed Jan. 25, 2019, which claims the benefit of U.S. Provisional Patent Application No. 62/621,942, filed Jan. 25, 2018, and entitled "METHOD AND SYSTEM FOR FLUENCE MATCHING IN PHOTOACOUSTIC IMAGING"; the entire contents of each of which are hereby incorporated by reference.

FIELD

Various embodiments are described herein that generally relate to PhotoAcoustic (PA) imaging, and in particular for hardware and methods that may be used to perform fluence matching in generated PA images.

BACKGROUND

PA imaging in biomedical fields has been one of the fastest growing modalities, as it can simultaneously deliver structural and functional information of vasculatures [1-2]. The high optical absorption and weak ultrasound scattering of soft tissues allow for real time images with high optical contrast at depths and resolutions that no other imaging modality has been able to accomplish.

Despite the numerous capabilities of the PA imaging modality [3], the main use of PA imaging in the biomedical field has focused on detecting the spatial distribution of the chromophores inside biological structures [2, 4-6]. Hemoglobin is the major optical absorbing molecule in tissue and can relay functional information through changes in its biochemical structures. Detecting endogenous chromophores like hemoglobin allows for the capability of creating oxygenation maps which can be crucial in detecting diseases and monitoring treatment efficacy [4, 6].

The generated PA images are governed by the absorbing molecules that are present in the sample and the optical illumination patterns. The absorption spectra of different forms of hemoglobin vary greatly when illuminating the sample using different optical wavelengths. By illuminating the sample with multiple wavelengths, estimation of the relative concentration of the chromophores can be achieved [7]. However, quantification of chromophores is hindered by the dependence of the light distribution on optical wavelength [8].

The internal parameters which govern light distribution in tissues are represented by the tissue's optical properties. The tissue's optical properties are divided into the absorption coefficient ($\mu_a$), the scattering coefficient ($\mu_s$) and the anisotropy parameter (g). All these parameters may change spatially and with optical wavelength [9]. These changes create a challenge in solving for the relative chromophore concentration, as both the estimated concentration of chromophores and the light distribution depend on the tissue's absorption coefficient.

Methods implemented to eliminate or reduce the effect of optical fluence on acquired PA images include intensity modulation of the PA signals with depth using a diffusion model [10-12] or Monte Carlo simulations [13], which require prior knowledge of tissue optical properties. Another method is an inverse iterative approach to match the measured PA image [14-22], but this is computationally intensive. Use of fluence eigenspectra can account for wavelength-dependent light attenuation [23, 24], but this increases the number of optical wavelengths required for imaging. Other methods include using a reference dye [25], using multiple light sources [18, 26-28], or using prior knowledge of the tissue optical properties [29], which can be impractical in biomedical imaging. Other methods include combining PA imaging with diffuse optical tomography [28], and machine learning to account for wavelength-dependent light attenuation [23-24].

Unmixing techniques are applied to the PA images after fluence correction to quantify the chromophores. Methods for unmixing samples with unknown chromophores and chromophores with distinct absorption characteristics compared to background (e.g. nanoparticles) can be found in references [30-33].

To detect endogenous chromophores, e.g. hemoglobin, linear spectral unmixing is used. Linear spectral unmixing assumes that the PA signals generated by a sample in response to light illumination are due to the linear combination of the optical absorbers and their concentration. Linear spectral unmixing outputs the spatial distribution of the chromophores [34]. However, using conventional techniques, the extinction coefficients of the chromophores present in the sample is needed. The extinction coefficients for hemoglobin are well known. For other chromophores, the extinction coefficients can be measured using a spectrophotometer.

Linear spectral unmixing has been used to quantify the relative concentration of oxyhemoglobin and deoxyhemoglobin which can be used to assess oxygen saturation ($sO_2$). Other methods include extraction of the ratio of PA image amplitude [44] and intraclass correlation which assumes each pixel is composed of only one absorber [45].

SUMMARY OF VARIOUS EMBODIMENTS

Various embodiments of PA imaging hardware and associated PA imaging methods that use fluence matching are provided according to the teachings herein.

In one broad aspect, at least one embodiment is provided herein for an imaging device for performing fluence compensation on a photoacoustic (PA) image of at least a portion of an object, the imaging device comprising a preprocessing stage that is configured to receive a set of reference RF acoustic response signals that were generated by the portion of the object when being illuminated with light having a reference wavelength, and a set of uncompensated RF acoustic response signals that were generated by the portion of the object when being illuminated with light having a non-reference wavelength. The pre-processing stage includes a beamformer for applying beamforming to generate preprocessed RF acoustic response signals comprising a set of preprocessed reference RF acoustic response signals and a set of preprocessed uncompensated RF acoustic response signals. The device further comprises a fluence compensation stage comprising: a segmentor to segment each preprocessed reference and uncompensated RF acoustic response signal into a set of reference segments and a set of uncompensated segments, respectively, using a set of overlapping spatial windows; a frequency transform block to perform a frequency transform on each set of reference segments and each set of uncompensated segments to generate corresponding sets of reference power spectra and corresponding sets of uncompensated power spectra, respectively; a filter stage that is configured to: generate a filter that corresponds to each uncompensated segment of each preprocessed uncompensated RF acoustic response signal by averaging several uncompensated power spectra obtained at a common spatial window for other uncompensated RF acoustic response signals at adjacent sensor positions to obtain an average uncompensated power spectrum, averaging several reference power spectra obtained at the common spatial window for corresponding reference RF acoustic response signals to obtain an average reference power spectrum and taking a ratio of the uncompensated power spectrum to the reference power spectrum; and filter each uncompensated segment of each preprocessed uncompensated RF acoustic response signal using the corresponding filters to generate compensated segments for each preprocessed uncompensated RF acoustic response signal; and a combiner to combine the compensated segments of each preprocessed uncompensated RF acoustic response signal to generate a set of fluence compensated RF acoustic response signals; and an image generator for generating the PA image of the portion of the object for the non-reference wavelength using the set of fluence compensated RF acoustic response signals.

In at least one embodiment, the preprocessing stage further comprises a noise reduction stage for reducing noise in the reference and uncompensated RF acoustic response signals prior to beamforming.

In at least one embodiment, first and second halves of the power spectra used for averaging are power spectra obtained for sensor positions to the left and right, respectively, of the sensor position for which the average power spectra is being determined.

In at least one embodiment, about 10 to 40 power spectra are averaged. In at least one embodiment, about 20 power spectra are averaged.

In at least one embodiment, the set of overlapping spatial windows are arranged along a depth direction for the RF acoustic response signals with an amount of overlapping between adjacent spatial windows defined by an overlap factor.

In at least one embodiment, the overlap factor is about 1% to 99%. In at least one embodiment, the overlap factor is about 50% to 70%.

In at least one embodiment, the filters are bandpass filters having a bandpass with a frequency range and amplitude values that are determined from the ratio of the uncompensated power spectrum to the reference power spectrum for the frequency range.

In at least one embodiment, the ratio of the uncompensated power spectrum to the reference power spectrum in the frequency range is approximated using a line of best fit.

In at least one embodiment, the frequency range corresponds to a response bandwidth of the transducer used to acquire the RF acoustic response signals.

In at least one embodiment, the imaging device further comprises a spectral decomposition stage that performs spectral decomposition using PA images that were generated from the set of reference RF acoustic response signals and one or more sets of compensated RF acoustic response signals that were fluence matched to the set of reference RF acoustic response signals to generate a spatial map of source generators that generated the RF acoustic response signals.

In at least one embodiment, the spectral decomposition comprises linear spectral unmixing.

In at least one embodiment, the object comprises a blood sample, and the spatial map of source generators comprises an oxygen saturation ($sO_2$) map.

In at least one embodiment, the imaging device performs at least one of displaying a fluence compensated PA image on a display and storing the fluence compensated PA image in a data store.

In at least one embodiment, the RF acoustic response signals are obtained from a data store or they are obtained using an ultrasound sensor.

In at least one embodiment, the device comprises at least one processor that is configured to operate as the preprocessing stage, the fluence compensation stage and the image generator.

In another broad aspect, at least one embodiment is provided herein for a method for performing fluence compensation on a photoacoustic (PA) image of at least a portion of an object, the method comprising: receiving a set of reference RF acoustic response signals that were generated by the portion of the object when being illuminated with light having a reference wavelength, and a set of uncompensated RF acoustic response signals that were generated by the portion of the object when being illuminated with light having a non-reference wavelength; applying beamforming to generate preprocessed RF acoustic response signals comprising a set of preprocessed reference RF acoustic response signals and a set of preprocessed uncompensated RF acoustic response signals; segmenting each preprocessed reference and uncompensated RF acoustic response signal into a set of reference segments and a set of uncompensated segments, respectively, using a set of overlapping spatial windows; performing a frequency transform on each set of reference segments and each set of uncompensated segments to generate corresponding sets of reference power spectra and corresponding sets of uncompensated power spectra, respectively; generating a filter that corresponds to each uncompensated segment of each preprocessed uncompensated RF acoustic response signal by averaging several uncompensated power spectra obtained at a common spatial window for other uncompensated RF acoustic response signals at adjacent sensor positions to obtain an average uncompensated power spectrum, averaging several reference power spectra obtained at the common spatial window for corresponding reference RF acoustic response signals to obtain an average reference power spectrum and taking a ratio of the uncompensated power spectrum to the reference power spectrum; filtering each uncompensated segment of each preprocessed uncompensated RF acoustic response signal using the corresponding filters to generate compensated segments for each preprocessed uncompensated RF acoustic response signal; combining the compensated segments of each preprocessed uncompensated RF acoustic response signal to generate a set of fluence compensated RF acoustic response signals; and generating the PA image of the portion of the object for the non-reference wavelength using the set of fluence compensated RF acoustic response signals.

In at least one embodiment, the method comprises reducing noise in the reference and uncompensated RF acoustic response signals prior to beamforming.

In at least one embodiment, the method comprises using first and second halves of the power spectra for averaging which are power spectra obtained for sensor positions to the left and right, respectively, of the sensor position for which the average power spectra is being determined.

In at least one embodiment, the method comprises averaging about 10 to 40 power spectra are averaged. In at least one embodiment, the method comprises averaging about 20 power spectra are averaged.

In at least one embodiment, the method comprises arranging the set of overlapping spatial windows along a depth direction for the RF acoustic response signals with an amount of overlapping between adjacent spatial windows defined by an overlap factor.

In at least one embodiment, the method comprises using an overlap factor that is about 1% to 99%. In at least one embodiment, the method comprises using an overlap factor that is about 50% to 70%.

In at least one embodiment, the method comprises implementing the filters as bandpass filters having a passband with a frequency range and amplitude values that are determined from the ratio of the uncompensated power spectrum to the reference power spectrum for the frequency range.

In at least one embodiment, the method comprises approximating the ratio of the uncompensated power spectrum to the reference power spectrum in the frequency range using a line of best fit.

In at least one embodiment, the method comprises defining the frequency range to correspond to a response bandwidth of the transducer used to acquire the RF acoustic response signals.

In at least one embodiment, the method further comprises performing spectral decomposition using PA images that were generated from the set of reference RF acoustic response signals and one or more sets of compensated RF acoustic response signals that were fluence matched to the set of reference RF acoustic response signals to generate a spatial map of source generators that generated the RF acoustic response signals.

In at least one embodiment, the method comprises implementing the spectral decomposition using linear spectral unmixing.

In at least one embodiment, the object comprises a blood sample, and the spatial map of source generators comprises an oxygen saturation ($sO_2$) map.

In at least one embodiment, the method comprises performing at least one of displaying a fluence compensated PA image on a display and storing the fluence compensated PA image in a data store.

In at least one embodiment, the method comprises obtaining the RF acoustic response signals from a data store or using an ultrasound sensor.

In at least one embodiment, the method comprising configuring the at least one processor to provide the preprocessing, the fluence compensation and the image generation.

In another broad aspect, at least one embodiment is provided herein for an imaging device for performing fluence compensation on a photoacoustic (PA) image of at least a portion of an object, wherein the imaging device comprises: a segmentor to segment a set of preprocessed uncompensated RF acoustic response signals associated with a non-reference wavelength and a set of preprocessed reference RF acoustic response signals associated with a reference wavelength that is different than the non-reference wavelength into a set of uncompensated segments and a set of reference segments, respectively, using a set of overlapping spatial windows; a filter stage that is configured to filter each uncompensated segment of each preprocessed uncompensated RF acoustic response signal using corresponding filters to generate compensated segments for each preprocessed uncompensated RF acoustic response signal where a given corresponding filter has a bandpass that is defined using a power spectra ratio of a given uncompensated power spectra related to the uncompensated segment with respect to a given compensated power spectra related to the compensated segment that is at a common spatial window to the uncompensated segment; a combiner to combine the compensated segments of each preprocessed uncompensated RF acoustic response signal to generate a set of fluence compensated RF acoustic response signals; and an image generator for generating the PA image of the portion of the object for the non-reference wavelength using the set of fluence compensated RF acoustic response signals.

In at least one embodiment, the given uncompensated power spectra is an average uncompensated power spectrum that is obtained by averaging several uncompensated power spectra obtained at a common spatial window for other uncompensated RF acoustic response signals at adjacent sensor positions and the given reference power spectrum is an average reference power spectrum obtained at the common spatial window for corresponding reference RF acoustic response signals.

In at least one embodiment, the given corresponding filter is a bandpass filter having a bandpass with amplitude values that are determined from a line of best fit of the uncompensated power spectrum to the reference power spectrum.

In another broad aspect, at least one embodiment is provided herein for a method for performing fluence compensation on a photoacoustic (PA) image of at least a portion of an object, wherein the method comprises: segmenting a set of preprocessed uncompensated RF acoustic response signals associated with a non-reference wavelength and a set of preprocessed reference RF acoustic response signals associated with a reference wavelength that is different than the non-reference wavelength into a set of uncompensated segments and a set of reference segments, respectively, using a set of overlapping spatial windows; filtering each uncompensated segment of each preprocessed uncompensated RF acoustic response signal using corresponding filters to generate compensated segments for each preprocessed uncompensated RF acoustic response signal where a given corresponding filter has a bandpass that is defined using a power spectra ratio of a given uncompensated power spectra related to the uncompensated segment with respect to a given compensated power spectra related to the compensated segment that is at a common spatial window to the uncompensated segment; combining the compensated segments of each preprocessed uncompensated RF acoustic response signal to generate a set of fluence compensated RF acoustic response signals; and generating the PA image of the portion of the object for the non-reference wavelength using the set of fluence compensated RF acoustic response signals.

In at least one embodiment, the method comprises determining the given uncompensated power spectra by obtaining an average uncompensated power spectrum by averaging several uncompensated power spectra obtained at a common spatial window for other uncompensated RF acoustic response signals at adjacent sensor positions and determining the given reference power spectrum by obtaining an average reference power spectrum at the common spatial window for corresponding reference RF acoustic response signals.

In at least one embodiment, the method comprises using a bandpass filter as the given corresponding filter where the bandpass filter has a bandpass with amplitude values that are determined from a line of best fit of the uncompensated power spectrum to the reference power spectrum.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 3B shows an example of the spatial positions of a set of RadioFrequency (RF) acoustic response signals acquired with a light stimulus $L_1$ at a given wavelength.

FIG. 3C shows an example of the spatial and temporal positions for a plurality of sets of RF acoustic response signals acquired with sequential light stimuli $L_1$ to $L_P$ each at the given wavelength.

FIG. 3D shows an example of spatial windowing that is done for a preprocessed RF acoustic response signal for a given sensor $S_i$.

FIG. 3E shows an example of the frequency transforms corresponding to the spatial windows used in segmentation for a subset of the sensor elements.

FIG. 3F shows an example of how compensated segments for an RF acoustic response signal can be recombined based on the spatial windowing.

FIG. 4A shows example RF acoustic response signals for which two PA images were derived.

FIG. 4B shows segments of the example RF acoustic response signals of FIG. 4A due to apply a spatial window between two ranges.

FIG. 4C shows an example of the average power spectrum of the RF acoustic response signals of FIG. 4A.

FIG. 4D shows an example of a difference of the two power spectra in log scale in FIG. 4C.

FIGS. 9A-9C show an example of PA images captured at a non-reference wavelength, spatial windows and corresponding power spectra and averaged power spectra.

FIGS. 9D-9F show an example of PA images captured at a reference wavelength, spatial windows and corresponding power spectra and averaged power spectra.

FIG. 10A shows the averaged power spectra of FIGS. 9A-9F.

FIG. 10B shows the power spectrum ratio and spectral slope of the averaged power spectra of FIG. 10A.

Figure 1:
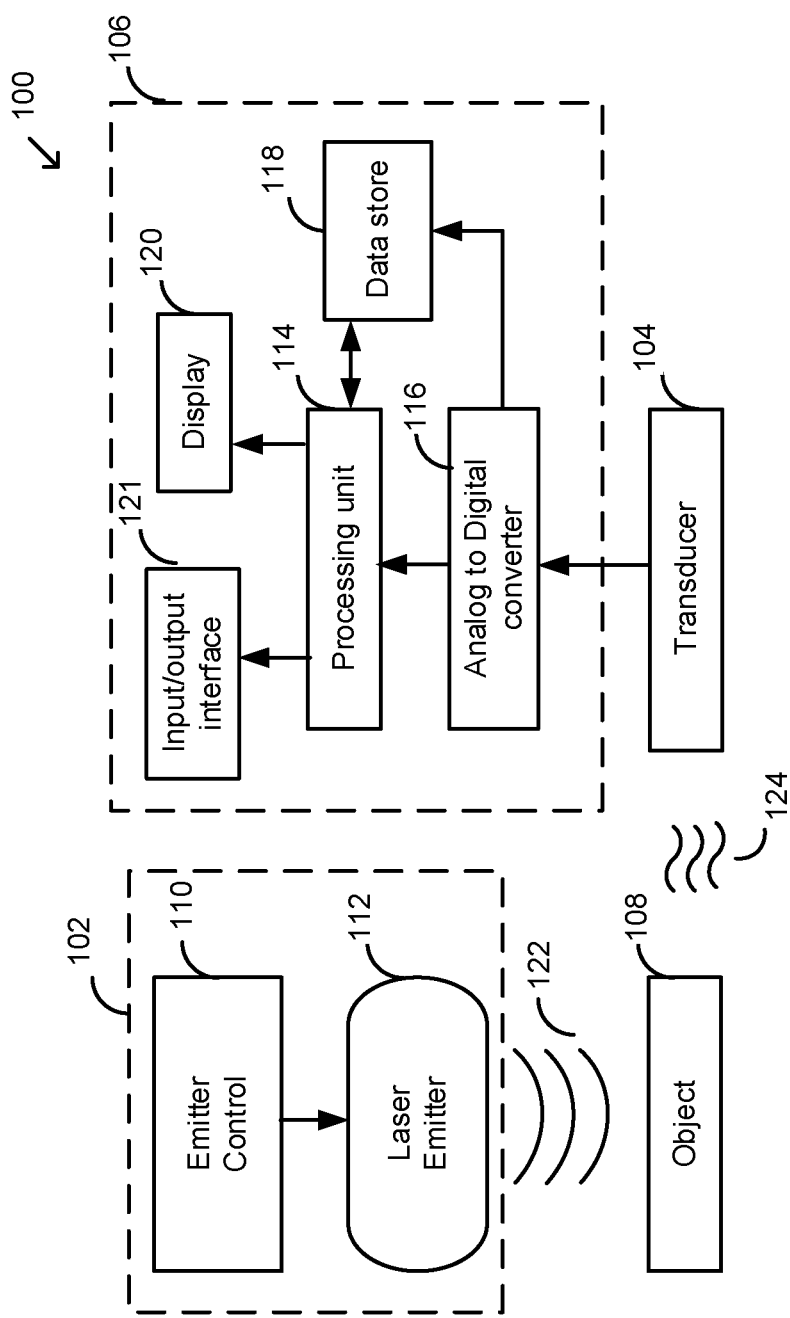
FIG. 1 is a block diagram of an example embodiment of a PA imaging system in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to some or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, optical or electrical connotation. For example, as used herein, the terms coupled or coupling can indicate that two elements or devices can be directly connected to one another or connected to one another through one or more intermediate elements or devices via an electrical or optical signal or a mechanical element, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e. at least one volatile memory element and at least one non-volatile memory element). The hardware may comprise input devices including at least one of a touch screen, a keyboard, a mouse, buttons, keys, sliders and the like, as well as one or more of a display, a speaker, a printer, and the like depending on the implementation of the apparatus.

It should also be noted that there may be some elements that are used to implement at least part of the embodiments described herein that may be implemented via software that is written in a high-level procedural language such as object oriented programming. The program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a computer readable medium such as, but not limited to, a ROM, a magnetic disk, an optical disc, a USB key and the like that is readable by a device having a processor, an operating system and the associated hardware and software that is necessary to implement the functionality of at least one of the embodiments described herein. The software program code, when read by the device, configures the device to operate in a new, specific and predefined manner in order to perform at least one of the methods described herein.

Furthermore, at least some of the programs associated with the devices, systems and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The following description and drawings illustrate example embodiments of at least one system, device and corresponding method that may be used to match the fluence profiles of the acquired PA images among imaged wavelengths. The inventors have discovered that changes in optical fluence can be extracted from the ratio of the power spectra that is obtained from RF signals that are generated by an object, such as a sample including, but not limited to, a tissue sample, for example, when it is illuminated with at least two optical signals having two different wavelengths. In accordance with the teachings herein, changes in the optical fluence for the imaged wavelengths are measured by assuming that the ultrasound generators among the imaged wavelengths are the same and the teachings herein compensate for changes in light distribution using associated frequency changes.

PA imaging involves the irradiation of tissues with short pulses of laser light. In response to the light stimulation, absorbers or chromophores in a sample, such as a tissue sample, will rapidly expand to create a pressure rise and gradually contract due to heat dissipation. The process is referred to as thermoelastic expansion, with an initial pressure rise ($p_0$) expressed as:

$$p_0(r')=\Gamma H(r',t') \quad (1)$$

where r' is the location of the absorbers, $\Gamma$ is Grüneisen parameter and H is the deposited thermal energy. The Grüneisen parameter may have a relatively small spatial fluctuation for a fixed temperature. Therefore, the Grüneisen parameter is usually assumed to be constant as the spatial fluctuations are insignificant [14]. The thermal energy deposited is the energy deposited per unit volume and per unit time and it is expressed as:

$$H(r',t')=\phi(r',t')\mu_a(r') \quad (2)$$

where $\phi$ is the light fluence and $\mu_a$ is the optical absorption coefficient. The pressure rise will generate ultrasound pulses or pressure waves that propagate according to the PA wave equation [38]. The deposited thermal heat determines the shape of the generated waves, since all other parameters will only contribute to the amplitude of the generated waves.

The generated PA signals can be detected using an ultrasound transducer (i.e. an ultrasound sensor). Since the generated PA signals have frequencies in the RF range, they may also be referred to herein as PA RF signals or RF acoustic response signals since the signals are acoustic signals with frequency content in the RF range. For ease of illustration, the detected PA RF signals contain information about the sample and the instrumentation used. The ultrasound power spectra for the received PA RF signal can be represented by:

$$E(f)=p(f)gD(f)^2BW(f)A(f) \quad (3)$$

where p is the generated pressure [38], g is the gating function, D is the directivity function of the transducer elements, BW is the bandwidth of the transducer, and A(r) is the ultrasound attenuation [39, 40]. To eliminate the effect of the system, the ratio of the power spectra of RF acoustic response signals that are generated when providing the sample with illumination at two different optical wavelengths (as employed in quantitative ultrasound imaging [35], [36], [41]) is shown below in equation 4.

$$\frac{E_{\lambda_1}(f)}{E_{\lambda_2}(f)} = \frac{p_{\lambda_1}(f)D^2(f)g(f)BW(f)A(f)}{p_{\lambda_2}(f)D^2(f)g(f)BW(f)A(f)} = \frac{p_{\lambda_1}(f)}{p_{\lambda_2}(f)} \quad (4)$$

In equation 4, the effect of the system is the same for both optical wavelengths and will be eliminated. However, the inventors have determined that the ratio of the power spectra carries information about the absorption coefficient and light fluence.

In PA imaging, the ultrasound source generators for tissue samples are dominated by hemoglobin molecules due to their high optical absorption at the visible and near infrared regime [40]. The RF acoustic response signals, also referred to herein as acoustic response signals, that are measured when illuminating the tissue sample with different optical wavelengths adds difficulty in order to accurately estimate $sO_2$ values at certain depths. This difficulty is inherent during data acquisition to the dependence of the illuminating light distribution with optical wavelength. This manifests itself as a change in optical fluence in the PA images with depth which mistakenly implies certain changes in the amplitude of the source generators (i.e. chromophores). The inventors have discovered that the amplitude alteration in the generated RF acoustic response signals in the underlying sample is due to the difference in light penetration within the sample at the different wavelengths and not due to the absorption of the chromophores. This dependence of light distribution with optical wavelength affects the accuracy in PA chromophore quantification. Therefore, $sO_2$ estimates, which depend on the distribution of the chromophores, may be inaccurate in-depth due to the lack of proper fluence compensation. In fact one major issue with assessing oxygen saturation through linear spectral unmixing has been a decrease in the apparent $sO_2$ value with depth. This problem is addressed in accordance with the teachings herein. For example, FIGS. 7A-7B show PA images obtained using two different wavelengths with differences in fluence change versus depth due to the different wavelengths that were used.

However, the inventors have determined that, by assuming the optical absorbing sources (i.e. source generators) are the same at different imaged wavelengths (i.e. the different wavelengths used when illuminating the sample), changes in the ratio of the power spectra for RF acoustic response signals as a function of frequency can be directly associated to the change in the optical fluence. Therefore, in accordance with the teachings herein, the measured changes in optical fluence can be used to match the fluence profile of the imaged wavelengths.

In accordance with the teachings herein, the changes in optical fluence can be inferred from the PA spectral slopes and used to generate frequency filters that can be applied to the acoustic response signals in such a way as to match the fluence across certain optical wavelengths. A technique has been developed, in accordance with the teachings herein, which takes this into account and the technique is referred to herein as fluence compensation or fluence matching. This methodology has the capability to improve the accuracy of spectral unmixing to assess oxygen saturation maps.

Referring now to FIG. 1, shown therein is a block diagram of an example embodiment of a PA imaging system 100 in accordance with the teachings herein. The PA imaging system 100 comprises a light source 102, a transducer 104 and a PA imaging device 106 that are used to generate PA images of an object 108. The object 108 may be a sample that requires analysis such as a biological sample or phantom studies, for example. The biological sample may be a tissue sample in some cases and phantom studies may include a gelatin vessel phantom.

The light source 102 comprises an emitter control 110 that is operably coupled to a laser emitter 112 to control it to generate light signals 122 at desired wavelengths for illuminating the object 108. One of the wavelengths is defined as being a reference wavelength and the other wavelengths are defined as being non-reference wavelengths. In some embodiments, the emitter control 110 may be operatively coupled to the imaging device 106 for receiving control signals therefrom. In some embodiments, other types of light generators may be used such as LEDs, for example. The emitter control 110 may be implemented by a processor or other suitable hardware. The implementation of the light source 102 components are generally known by those skilled in the art.

The imaging device 106 comprises a processing unit 114, an Analog to Digital Converter 116 (ADC), a data store 118, a display 120 and an input/output interface 121 which may be coupled to various peripheral components (not shown). In some embodiments, the processing unit 114 may also provide the functionality of the emitter control 110. The imaging device 106 may also include a power unit (not shown) or be connected to a power source to receive power needed to operate its components. It should be noted that the components shown in FIG. 1 are provided as an example and there may be more or less components or alternative layouts in other embodiments.

The processing unit 114 is operatively coupled to the other components of the imaging device 106 for controlling various operations of the imaging device 106, such as the data acquisition process (i.e. controlling sampling rates and sampling periods), the energy normalization for the laser emitter 112 and the operation of fluence compensation methods. The processing unit 114 can be any suitable processor, controller or digital signal processor that can provide sufficient processing power depending on the operational requirements of the device 106 as is known by those skilled in the art. For example, the processing unit 114 may be a high performance general processor. In alternative embodiments, the processing unit 114 may include more than one processor with each processor being configured to perform different dedicated tasks. In alternative embodiments, specialized hardware can be used to provide some of the functions provided by the processing unit 114, such as at least one Application Specific Integrated Circuit (ASIC) and/or a Field Programmable Gate Array (FPGA), for example.

The data store 118 includes volatile and non-volatile memory elements such as, but not limited to, one or more of RAM, ROM, one or more hard drives, one or more flash drives or some other suitable data storage elements. The data store 118 may be used to store an operating system and programs as is commonly known by those skilled in the art. For instance, the operating system provides various basic operational processes for the processing unit 114 and the programs include various operational and user programs so that a user can interact with the processing unit 114 to configure control and configure the device 106.

The data store 118 may also include software code for implementing various components for performing fluence compensation in accordance with the teachings herein as well as values of various operational parameters that are used in fluence compensation. The data store 118 can also be used to store the RF acoustic response signals that are acquired, various processed forms of these signals and any images that are generated therefrom such as PA images or oxygenation maps, for example. The data store 118 may also include one or more databases for storing the information.

The display 120 can be any suitable device for displaying images and various types of information such as an LCD monitor or touchscreen display. The input/output interface 121 can be various ports such as one of more of USB, Firewire, serial and parallel ports, for example, that may be coupled with various peripheral devices used for the input or output of data. Examples of these devices include, but are not limited to, at least one of a keyboard, a mouse, a trackpad, a touch interface, and a printer.

In use, the laser emitter 112 is controlled to generate light signals 122 for illuminating the object 108. The light signals 122 are generated to have a predetermined waveform at a predetermined wavelength for a predetermined period of time for eliciting an RF acoustic response signal from the object 108 as is known by those skilled in the art. In fact the laser emitter 112 can be controlled to generate at least two light signals 122 having a different wavelength in a sequential fashion in time to elicit corresponding acoustic response signals 124 from the object 108 that are generated due to the thermoelastic expansion process explained previously. The light emitter 112 can generate several light signals 122 that each have a unique one of the stimulus wavelengths so that multiple corresponding RF acoustic response signals 124 can be acquired from the object 108 and processed to obtain more accurate results.

The RF acoustic response signals 124 are sensed by the transducer 104 which is an ultrasonic transducer having an array of ultrasound sensors, as is known by those skilled in the art. For example, the transducer 104 can be a linear array transducer. In some embodiments, the transducer 104 may be a phased array transducer. The RF acoustic response signals 124 have informative frequency content in the RF range. Accordingly, the transducer 104 is designed with a frequency response bandwidth in the RF range so that it can sense the RF acoustic response signals that are generated by the object when it is illuminated with light stimuli.

During data acquisition, the RF acoustic response signals that are sensed by the transducer 104 are converted to digital signals by the ADC 116. The RF acoustic response signals can then be stored in the data store 118 for later processing or can be sent to an input (not shown) of the processing unit 114 which processes the RF acoustic response signals to generate fluence compensated RF acoustic response signals that may be used to generate fluence compensated PA images or may be used to show a property map of a certain property of the object such as oxyhemoglobin maps when the object is a tissue sample, for example. The processing unit 114 may also generate images, such as the PA images, without applying fluence compensation in certain cases. The methodology for performing fluence compensation is described in more detail with respect to FIGS. 2 and 3A-3E. The generated PA images can then be stored in the data store 118. The fluence compensated PA images, the fluence uncompensated PA images, the RF acoustic response signals, the compensated RF acoustic response signals and/or one or more property maps can be shown on the display 120 and/or stored in the data store 118.

Figure 2:
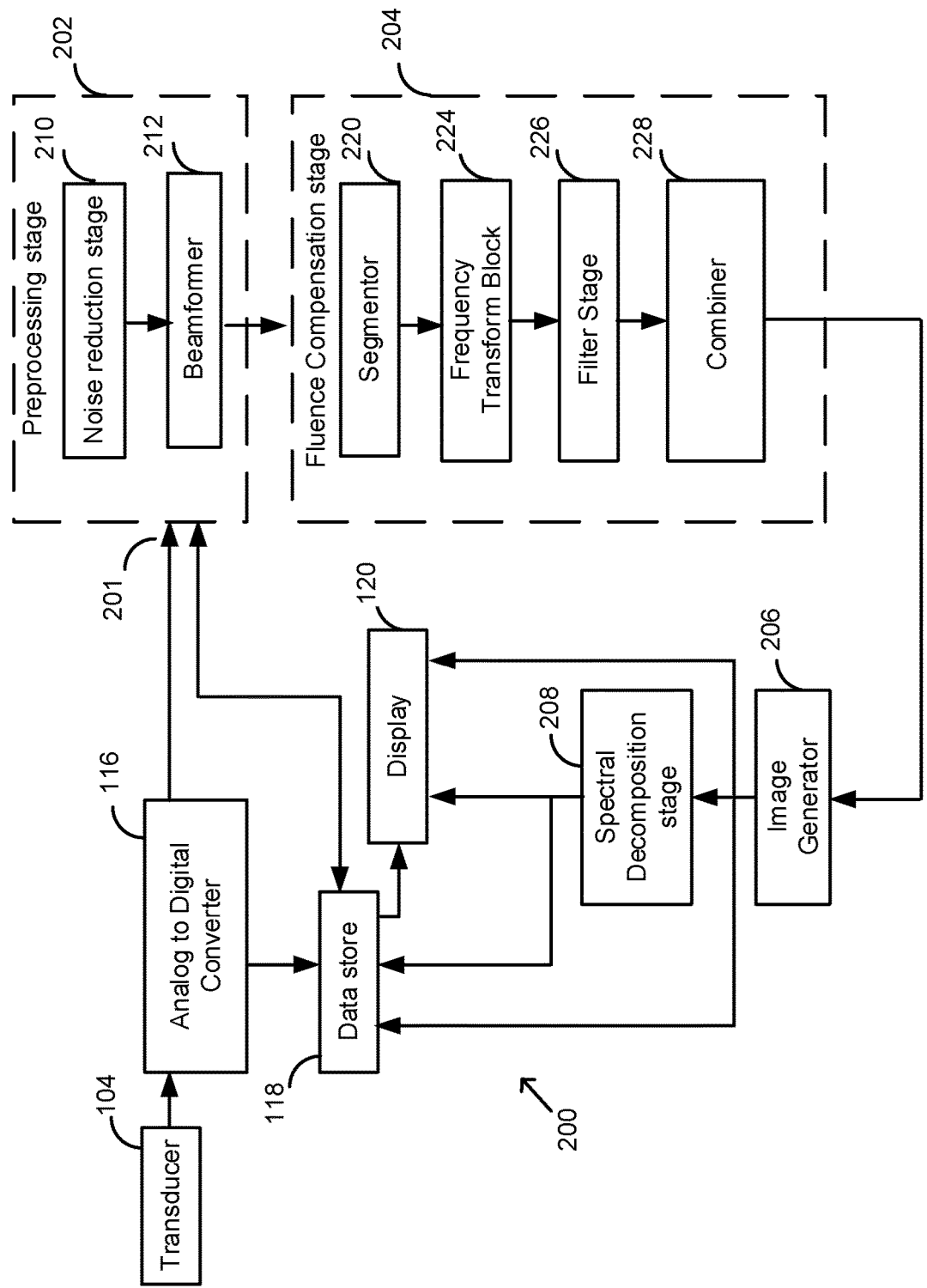
FIG. 2 is a block diagram of an example embodiment of an imaging device that can perform fluence compensation in accordance with the teachings herein.
Figure 3A:
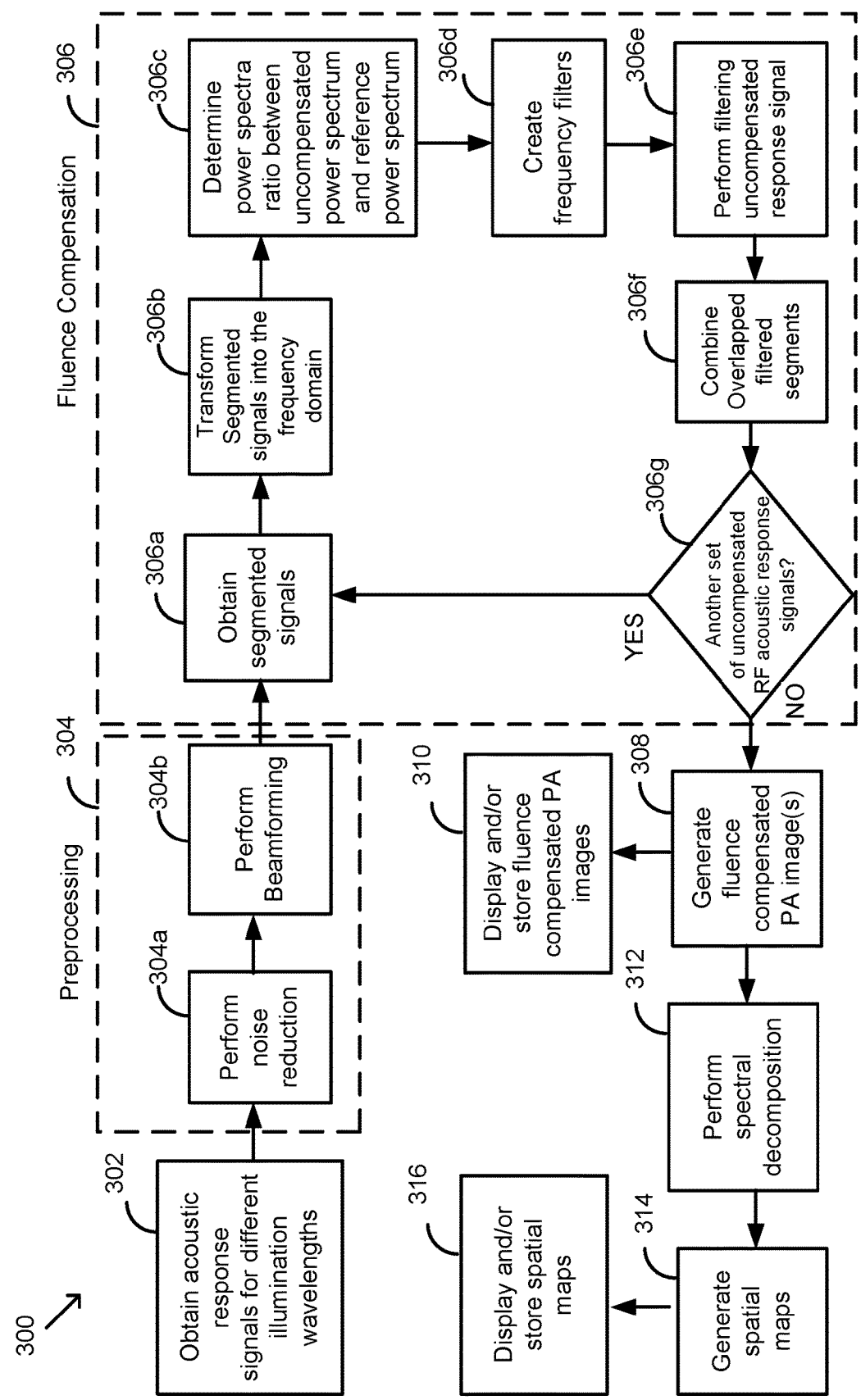
FIG. 3A is a flow chart diagram showing an example embodiment of a PA imaging method in accordance with the teachings herein.

Referring now to FIGS. 2 and 3A, shown therein is a block diagram of an example embodiment of an imaging device 200 and a corresponding fluence compensation method 300 that can be applied to obtain fluence compensation in accordance with the teachings herein. The imaging device 200 comprises a preprocessing stage 202, and a fluence compensation stage 204 that can be used with the transducer 104, the ADC 116, the data store 118, the display 120 and the input output interface 121 (not shown) of the PA imaging system 100 to generate fluence compensated RF acoustic response signals. The device 200 also comprises an image generator 206 for generating PA images with or without fluence compensation images. The device 200 may also include a spectral decomposition stage 208 (which is optional) that can be used to generate a property map of a property of the object 108, such as an oxyhemoglobin map with fluence compensation, for example. In some embodiments, the imaging device 200 may include the ADC 116, the data store 118 and the display 120. In some embodiments, the imaging device 200 may also include the transducer 104.

At act 302 of fluence compensation method 300, the imaging device 200 obtains a plurality of RF acoustic response signals comprising a set of reference RF acoustic response signals that were generated by a portion of the object 108 when it was illuminated with light having a reference wavelength, and a set of uncompensated RF acoustic response signals that were generated by the portion of the object 108 when it was illuminated with light having a non-reference wavelength. In some embodiments, there can be multiple sets of uncompensated RF acoustic response signals where each set of uncompensated RF acoustic response signals were generated by the portion of the object 108 when it was illuminated with light having a non-reference wavelength which is a wavelength that is not the same as the reference wavelength.

Fluence compensation is performed on the uncompensated RF acoustic response signals at a set of sensor positions with respect to corresponding reference RF acoustic response signals that correspond to the same sensor positions to obtain a set of fluence compensated RF acoustic response signals that are fluence matched to corresponding reference RF acoustic response signals. Therefore, when there are 2 different chromophores of interest, spectral decomposition (such as linear spectral unmixing) can be performed using two sets of RF acoustic response signals comprising one set of reference RF acoustic response signals and one set of corresponding fluence compensated RF acoustic response signals, where fluence compensation is performed in accordance with the teachings herein to obtain a more accurate spectral decomposition and therefore more accurate spatial data for the chromophores.

In general, when there are Y different chromophores where Y has an integer value that is greater than or equal to 2, then Z sets of RF acoustic responses signals can be acquired where Z has an integer value and $Z>=Y$. One of the Z sets of RF acoustic response signals can be defined as a set of reference RF acoustic response signals and the remaining Z-1 sets of RF acoustic response signals can be defined as being sets of uncompensated RF acoustic response signals. When $Z>Y$, fluence compensation can be performed on the Z-1 sets of uncompensated RF acoustic response signals to obtain Z-1 sets of fluence compensated RF acoustic response signals. The Z-1 sets of fluence compensated RF acoustic response signals and the set of reference RF acoustic response signals can then be used to obtain spatial data on the Y chromophores by performing various spectral decomposition techniques (such as linear spectral unmixing, for example). The value of Z can be set to be greater than the value of Y in certain cases where it will improve the spectral decomposition results.

The RF acoustic response signals that are processed may be received from the data store 118 for post data acquisition processing and possibly PA image generation. Alternatively, the RF acoustic response signal can be received from the transducer 104 via the ADC 116 (as was described in relation to FIG. 1) for performing real-time fluence compensation. In this case, the RF acoustic response signals sensed by the transducer 104 are converted into digital signals 201 by the ADC 116. At this point, the RF acoustic response signals may also be stored at the data store 118. In both input scenarios, the RF acoustic response signals that will be processed for fluence compensation are digital signals 201.

The preprocessing stage 202 generally includes a beamformer 212. At act 304, the preprocessing stage 202 receives a set of reference RF acoustic response signals that were generated by the portion of the object 108 when it was illuminated with light having a reference wavelength, and a set of uncompensated RF acoustic response signals that were generated by the portion of the object 108 when it was illuminated with light having a non-reference wavelength and performs preprocessing on these signals.

The RF acoustic response signals can be organized in a 2D manner similar to that shown in FIG. 3B where the transducer 104 has a linear array of M ultrasound sensors. The RF acoustic response signals are sampled for each sensor $S_i$ over time when illuminating the object 108 with a stimulus light signal $L_1$ having an illumination wavelength. These RF acoustic response signals can be collectively referred to as a set of RF acoustic response signals. The time value that each sample of an RF acoustic response signal was obtained is converted to a depth $D_i$ value by multiplying the sample time with the speed of light. The data from subsequent light stimulus stimuli can be organized as other 2D data sets which together can be organized as a 3D data set for light stimuli $L_1$ to $L_P$ as shown in FIG. 3C.

There are separate sets of RF acoustic response signals for light stimuli that have different wavelengths. Accordingly, the set of RF acoustic response signals obtained with a light stimuli having a reference wavelength are organized as a first data set for one light stimuli as shown in FIG. 3B or for multiple light stimuli as shown in FIG. 3C. Likewise each set of RF uncompensated acoustic response signals obtained with different non-reference wavelength are organized as other data sets that can be 2D or 3D. There may be more than one set of RF uncompensated acoustic response signals as explained previously.

At act 304b, the preprocessing stage 202 applies beamforming to generate preprocessed RF acoustic response signals comprising a set of preprocessed reference RF acoustic response signals and a set of preprocessed uncompensated RF acoustic response signals. The beamforming can be done in several ways. For example, when the transducer 104 has a linear array of ultrasound sensors, the delay and sum method can be used to perform beamforming using a sliding window on a subset of response data from the different ultrasound sensors. For example, there can be 256 ultrasound sensors, and the sliding window can be defined to include the data from 64 ultrasound sensors and the beamformed value for a given sensor $S_i$ includes a delay waited sum of the values sensed from sensor number $S_{i-32}$ to sensor number $S_{i+32}$ when such sensors exist. This is be repeated for each depth position to obtain a 2D data set, such as the data set shown in FIG. 3B.

In some embodiments, the preprocessing stage 202 may also include a noise reduction stage 210 that can be used to perform certain signal enhancement operations prior to beamforming at act 304a. The signal enhancement operations include at least one of as amplification and/or time averaging to improve the signal to noise Ratio (SNR). The noise reduction stage 210 may be optional when the acquired RF acoustic response signals have sufficient SNR for further processing.

In this case time averaging may be done for data obtained for the same depth position using successive light pulses in the light stimuli. For example, referring to FIG. 3C shown therein is a 3D data set where each vertical slice of data is obtained for a given light stimulus Li where the light stimulus are applied sequentially in time. For a given sensor Si time averaging can be done by averaging the values across the different light stimuli for a given depth position Di.

An uncompensated PA image can be generated using a set of preprocessed uncompensated RF acoustic response signals obtained with a non-reference wavelength. The pixel locations of the uncompensated PA image are defined by x,y coordinates where the y coordinate corresponds to one of the depth positions (i.e. one of the $D_i$) and the x coordinate corresponds to a position of one of the sensors (i.e. one of the $S_i$) since the array of sensor elements are physically spaced over a certain horizontal distance. The amplitude at a given pixel location can be taken to be a logarithmic value of the envelope of the preprocessed uncompensated RF acoustic response signal that corresponds with the depth and sensor positions associated with the given pixel location.

The fluence compensation stage 204 comprises a segmentor 220, a frequency transform block 224, a filter stage 226 and a combiner 228. At act 306 of fluence compensation method 300, the fluence compensation stage 204 performs fluence compensation on the sets of preprocessed RF acoustic response signals to obtain fluence compensated RF acoustic response signals. The fluence compensation that is performed by the fluence compensation stage 204 may also be referred to as fluence matching one or more sets of RF acoustic response signals corresponding to one or more PA images that were obtained using one or more non-reference wavelengths to one set of RF acoustic response signals corresponding to another PA image that were obtained using the reference wavelength. The fluence compensation stage 204 may be implemented using software modules with programming code that is executed by at least one processor or at least some components of the fluence compensation stage 204 may be implemented using other suitable hardware that can provide faster and more efficient computation such as, but not limited to, an ASIC, an FPGA or a Graphics Processing Unit (GPU), for example, due to the RF acoustic signals having a very large number of samples that are processed.

At act 306a of fluence compensation method 300, the segmentor 220 is used to segment each the RF each preprocessed reference and uncompensated RF acoustic response signal into a set of reference segments and a set of uncompensated segments, respectively, using a set of overlapping spatial windows. The size of the spatial window can be defined based on at least one of the wavelengths in the response bandwidth of the transducer. For example, the size of the spatial window can be a multiple of one of the wavelengths in the response bandwidth such as 10 times the longest wavelength in the response bandwidth of the transducer 104. For example, a spatial window size may be 1.6 mm. In another example, as was done in the study described below, the spatial window size may be 1.80 mm or 0.77 mm.

Referring now to FIG. 3D, shown therein is an example of spatial windowing that is done for a preprocessed RF acoustic response signal for a given sensor $S_i$ using spatial windows $W_1$ to $W_K$ that overlap according to an overlap factor. The overlap factor defines the percentage of a subsequent spatial window (e.g. $W_2$) that overlaps a previous spatial window (e.g. $W_1$). Only one of the spatial overlaps (OV) is identified in FIG. 3D for simplicity. The overlap factor can extend for 1% to 99% with a higher overlap factor resulting in better fluence compensation as the fluence changes at various depth positions. However, a higher overlap factor results in greater amount of computations and more processing time. The inventors have found that an overlap factor in the range of about 50% to 70% provides good fluence compensation results although the overlap factor may be set to be other values in other embodiments as different values for the overlap factor may be more suitable to obtain better fluence compensation for different types of objects 108 that are being PA imaged. For the example study results shown in FIGS. 7, 11, and 13, an overlap of 66% was used.

At act 306b of fluence compensation method 300, the frequency transform block 224 performs a frequency transform on each set of reference segments and each set of uncompensated segments to generate corresponding sets of reference power spectra and corresponding sets of uncompensated power spectra, respectively. The frequency transform may be implemented by using the Fast Fourier Transform. In other embodiments, other frequency transforms may be used such as the Wavelet transform, for example.

Referring now to FIG. 3E, shown therein is an example of the frequency transforms corresponding to the spatial windows used in segmentation for a subset of the sensor elements. For example, for the reference segments obtained using spatial windows $W_1$ for sensors $S_{i-q}$ to $S_{i+q}$ there will be frequency transforms $F_{i-q}$ to $F_{i+q}$. This is repeated for the other spatial windows for the reference segments. The same is true for each uncompensated segment of the one or more sets of uncompensated RF acoustic response signals.

The filter stage 226 performs acts 306c to 306f of fluence compensation method 300. At acts 306c and 306d, the filter stage 226 generates filters that correspond to each uncompensated segment of each preprocessed uncompensated RF acoustic response signal obtained at one of the non-reference wavelengths.

Referring again to FIG. 3E, at act 306c, for a given uncompensated segment at a given spatial window (e.g. the segment of the preprocessed RF acoustic response signal at a sensor position for sensor $S_i$ at spatial window $W_1$), the filter stage 226 averages the power spectrum ($F_1$) of the uncompensated segment with several uncompensated power spectra ($F_{i-q}$ to and $F_{i-1}$ to $F_{i+q}$) obtained at a common spatial window (i.e. the same spatial window as the given spatial window $W_1$) of other uncompensated RF acoustic response signals at adjacent sensor positions on either side of the current sensor position (e.g. $S_i$), such as for sensor positions for sensors $S_{i-q}$ to $S_{i-1}$ and $S_{i+1}$ to $S_{i+q}$, for example, to obtain an average uncompensated power spectrum. For example, q may be set to 10 so that there are 21 power spectra that are averaged together. In other embodiments, the parameter q may be set between 10 and 40. The filter stage 226 then averages several reference power spectra obtained at the common spatial window (e.g. $W_1$) for corresponding reference RF acoustic response signals at the same adjacent sensor positions to obtain an average reference power spectrum for the corresponding reference segment (e.g. the segment of the preprocessed RF acoustic response signal at position $S_1$ at spatial window $W_1$).

At act 306d, the filter stage 226 then creates a filter by taking a ratio of the average uncompensated power spectrum to the average reference power spectrum. This ratio can be referred to as a power spectrum ratio. The filter has a bandwidth that corresponds to the response bandwidth of the transducer 104 between a first frequency $F_L$ and a second frequency $F_H$. For example, the response bandwidth of the transducer 104 can be 8.5 to 30 MHz, but can be other values in other embodiments. The amplitude of the filter transfer function for frequencies lower than $F_L$ and higher than $F_H$ can be set to 0 thereby defining two stopbands. Accordingly, the filter is a bandpass filter and has a forced zero y-intercept. The amplitude of the filter transfer function between the frequencies $F_L$ and $F_H$ provides for the fluence compensation and can be an approximation of the values of the power spectrum ratio between the frequencies $F_L$ and $F_H$. For example, the values of the filter transfer function between frequencies $F_L$ and $F_H$ can be antilog values that approximate the power spectrum ratio between the same frequencies. An example of a filter is shown in FIG. 4E. The filters that are created using this technique carry information about the ratio of the optical fluence profiles at the non-reference imaged wavelength with respect to the reference imaged wavelength. It should be noted that in other embodiments, other filtering techniques that perform this type of filtering may be used in the time or frequency domain.

Acts 306c and 306d are repeated at each uncompensated segment of each preprocessed uncompensated RF acoustic response signal and therefore different filters are created at each spatial window for each uncompensated RF acoustic response signal.

At act 306e of the fluence compensation method 300, the filter stage 226 then filters each uncompensated segment of each preprocessed uncompensated RF acoustic response signal using the corresponding filter to generate compensated segments for each preprocessed uncompensated RF acoustic response signal that are in the spatial domain. The filtering can be done in the frequency domain and the filtered result can be converted to the spatial domain using an inverse frequency transform, such as an Inverse Fast Fourier Transformation, for example. Alternatively, the filtering may be done in the spatial domain by creating a spatial filter based on the transfer function of the filter in the frequency domain as is known by those skilled in the art.

At act 306f of the fluence compensation method 300, the combiner 228 combines the compensated segments of each preprocessed uncompensated RF acoustic response signal to generate a set of compensated RF acoustic response signals. Averaging is used to combine the overlap portions of the compensated segments of each uncompensated RF acoustic response signal after these compensated segments are aligned in the spatial domain. At act 306g of the fluence compensation method 300, it is determined whether there is another set of uncompensated RF acoustic response signals for the fluence compensation stage 204 to perform fluence compensation on. If this is true, the fluence compensation method 300 returns to act 306a. If this is not true, the method 300 proceeds to act 308.

Referring now to FIG. 3F, shown therein is an example of how compensated segments for an RF acoustic response signal can be recombined based on the spatial windowing to generate a compensated RF acoustic response signal. In this example, the spatial windows are overlapped such that each spatial window is shifted by one sample compared to a previous spatial window. The compensated segments are aligned in the spatial domain as shown and then averaged. Therefore, when determining the value at spatial location D1 for the compensated RF acoustic response signal, the value is just the sample Seg1,1 since there is no overlap. For determining the value at spatial location D2 for the compensated RF acoustic response signal, the value is the average of the samples Seg1,2 and Seg2,1 since there is an overlap of two samples at this spatial location. For determining the value at spatial location D3 for the compensated RF acoustic response signal, the value is the average of the samples Seg1,3, Seg2,2 and Seg3,1 since there is an overlap of three samples at this spatial location. The rest of the values of the compensated RF acoustic response signal are determined in a likewise fashion depending on the number of samples at each spatial location.

Figure 4F:
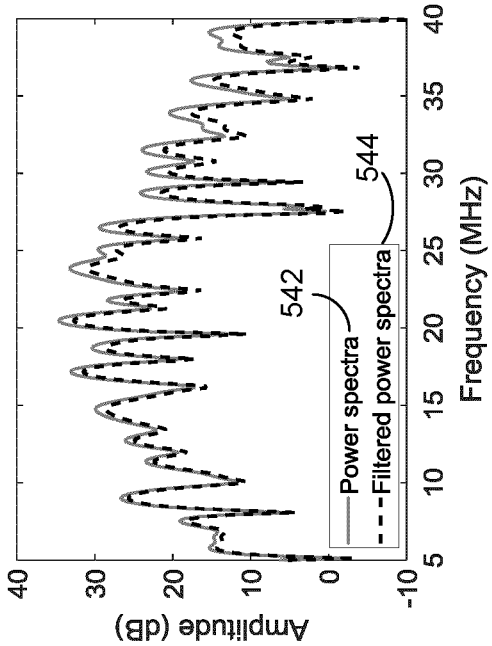
FIG. 4F shows an example of the power spectrum of one segment of an RF acoustic response signal prior to filtering during fluence compensation and an example of a compensated power spectrum of the same segment of the RF acoustic response signal after filtering.
Figure 4E:
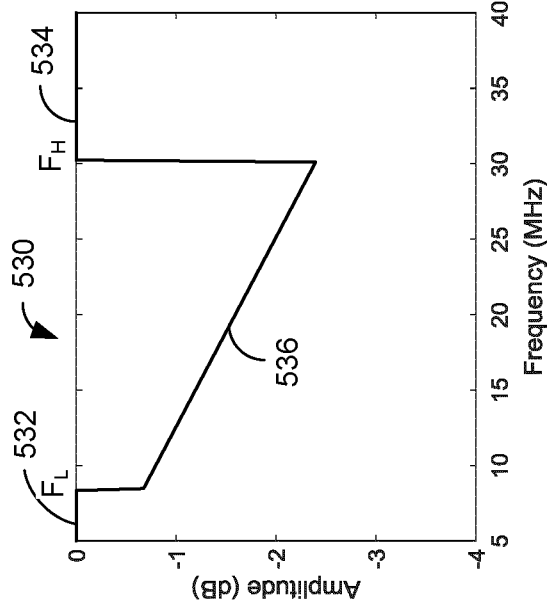
FIG. 4E shows an example of a frequency filter created from the difference power spectra of FIG. 4D and which can be used to obtain a compensated power spectra for one of segments of the uncompensated RF acoustic response signal of FIG. 4A.

As an example, referring now to FIGS. 4A-4G, shown in FIG. 4A is an example of two RF acoustic response signals 502 and 504 that correspond to the same sensor location for two PA images Image 1 and Image 2 that were obtained for light stimuli having wavelengths of 750 and 850 nm, respectively. Each of these signals 502 and 504 are normalized by the largest amplitude value in each signal. The RF acoustic response signal 504 is treated as a reference and the RF acoustic response signal 502 will be fluence matched to the RF acoustic response signal 504. The spatial depth of the signals 502 and 504 ranges from 9.5 mm to 13.5 mm.

FIG. 4B shows an uncompensated segment 502s and a reference segment 504s of the two signals 502 and 504 for the same spatial window 510, and these segments are generated when act 306a of the fluence compensation method 300 is performed.

FIG. 4C shows an uncompensated power spectrum 502ps and a reference power spectrum 504ps that correspond to the uncompensated segment 502s and the reference segment 504s which these power spectra are generated when act 306b of the fluence compensation method 300 is performed.

FIG. 4D shows an example of the power spectrum ratio 520 between the uncompensated power spectrum 502ps and a reference power spectrum 504ps. The plot in FIG. 4D is actually shown as a difference in the power spectra 502ps and 504ps since they are shown in a logarithm format and a ratio of two values in logarithm format is a difference of the two values.

The power spectrum ratio 520 is generated when act 306c is performed. FIG. 4D also shows a line of best fit 522 along a portion of the power spectrum ratio 520 that corresponds to the bandwidth of the transducer 104. The bandwidth of the transducer extends from frequency $F_L$ up to frequency $F_H$. The line of best fit 522 can be referred to as a spectral slope which is used in generating a filter.

The spectral slope (SS) includes information about the absorbers' size and the light distribution. When performing PA imaging on the same object using different optical wavelengths, the SS-estimated size in principle may remain unchanged assuming the same absorbers among the different imaged wavelengths. This suggests that any changes in the measured SS as a function of optical wavelength can be attributed to the light distribution and the spectral slope is directly correlated to this light distribution. Therefore, in accordance with the teachings herein, a frequency filter that is created using the determined SS can be used to provide fluence compensation in PA imaging. Based on the spatial averaging used in the example embodiment described herein, the determined spectral slope is a cumulative sum of the spectral slopes for each depth.

FIG. 4E shows the generated frequency filter 530 which has a stop band region 532 below the frequency $F_L$, a stop band region 534 above the frequency $F_H$ and an attenuation region 536 where the slope of the region 536 corresponds to the spectral slope 522. The filter 530 corresponds to the spatial window 510 for the segment 502s of the RF acoustic response signal 502. While a line of best fit 522 was used to generate the filter transfer function, in other embodiments other methods can be used to define the filter 530. For example, fluence compensation may alternatively be done in the time domain in alternative embodiments. The generation of the line of best fit 522 and the filter transfer function is done when act 306d of the fluence compensation method 300 is performed.

FIG. 4F shows an example of a power spectrum 542 of a segment of an RF acoustic response signal prior to the filtering done during fluence compensation and an example of a compensated power spectrum 544 of the same segment of the RF acoustic response signal after filtering. The filtering is done when act 306e of the fluence compensation method 300 is performed.

Figure 4G:
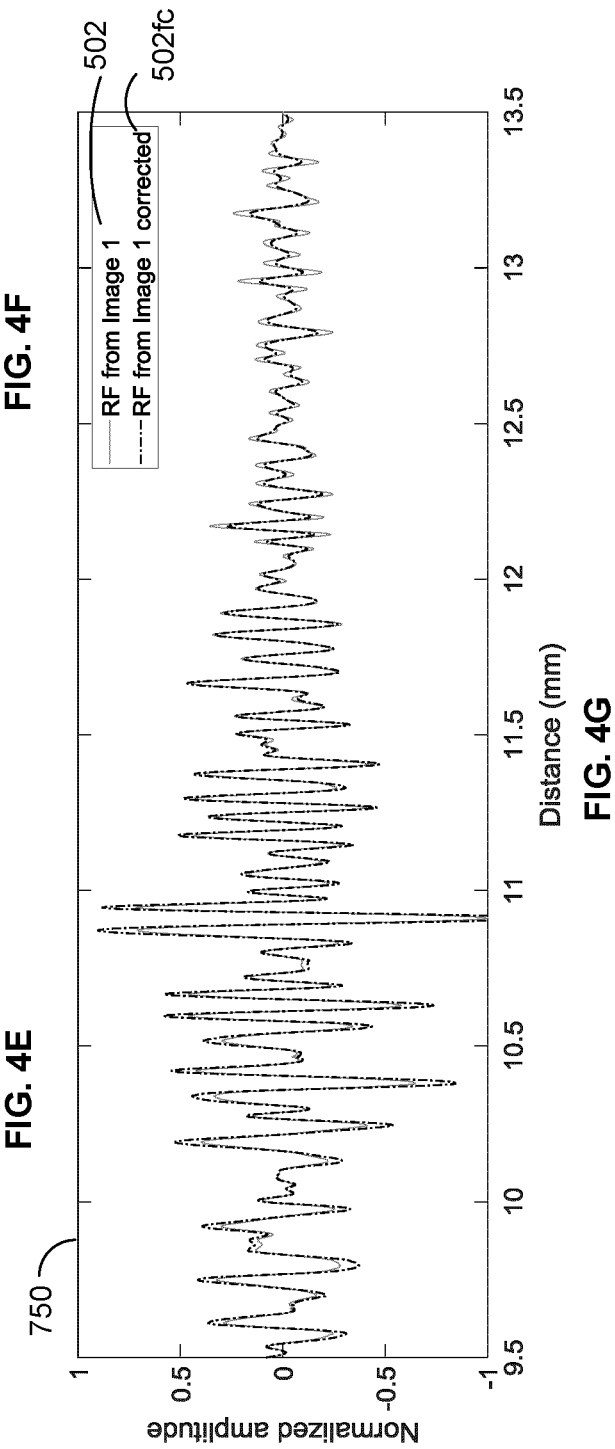
FIG. 4G shows an example of the RF acoustic response signal for a PA image 1 before and after fluence compensation.

FIG. 4G shows a pllot 750 of an example of the RF acoustic response signal 502 for the PA image 1 before fluence compensation. FIG. 4G also shows an example of a corresponding fluence compensated RF acoustic response signal 502fc. This fluence compensated signal is created when act 306f of the fluence compensation method 300 is performed.

In FIGS. 4F and 4G it can be seen that the decrease in the amplitude of the power spectra after fluence compensation is reflected in the compensated RF acoustic response signal in the spatial domain. Therefore, more negative SS values have more impact to the amplitude of the RF acoustic response signal.

Referring again to FIGS. 2 and 3A, at act 308 of the method 300, the image generator 206 can generate a fluence compensated PA image of the portion of the object 108 for a non-reference wavelength using the corresponding set of fluence compensated RF acoustic response signals. The pixel locations of the fluence compensated PA image are defined by x,y coordinates where the y coordinate corresponds to one of the depth positions (e.g. one of the $D_i$ in FIG. 3B) and the x coordinate corresponds to a position of one of the sensors (e.g. one of the $S_i$ in FIG. 3B) since the array of sensor elements are physically spaced over a certain horizontal distance. The amplitude at a given pixel location can be taken to be a logarithmic value of the envelope of the compensated RF acoustic response signal that corresponds with the depth and sensor positions associated with the given pixel location. A fluence compensated PA image can be generated for each set of RF acoustic response signals that were obtained using non-reference wavelengths. In some embodiments, the image generator 206 can also generate a PA image of the set of reference RF acoustic response signals in a similar manner. In some embodiments, the image generator 206 may crop the PA images since results along the edges of the image may be less reliable and more noisy for both uncompensated and fluence compensated PA images. One or more of the generated fluence compensated and/or fluence uncompensated PA images can be displayed on the display 120 and/or stored in the data store 118 at act 310 of the method 300.

At act 312 of the method 300, the spectral decomposition stage 208 performs spectral decomposition using PA images that were generated from the set of reference RF acoustic response signals and one or more sets of compensated RF acoustic response signals that were fluence matched to the set of reference RF acoustic response signals. In some embodiments, the spectral decomposition stage 208 may use cropped PA images in order to remove noisier samples as mentioned previously and obtain more accurate results. The spectral decomposition provides spatial data, such as a spatial distribution, which may be shown in a spatial map, of the source generators that generated the RF acoustic response signals during light stimulation. At act 314 of the method 300, the spatial maps may be generated. At act 316 of the method 300, the spatial maps may be displayed and/or stored. For example, if the object 108 is a tissue sample then spectral decomposition may be used to quantify the sO2 in the tissue sample by generating an sO2 map. One example of a spectral decomposition technique that may be used is linear spectral unmixing. In some embodiments, the PA images may be thresholded prior to spectral decomposition in order to reduce noise. For example, the PA images may be thresholded using Otsu's threshold [42] or another suitable threshold.

An example embodiment for performing linear spectral unmixing is now described. For a selected wavelength ($\lambda 1$), equation (2) can be rewritten as:

$$H_{\lambda_1}(r',t') = \phi_{\lambda_1}(r',t')[C_{HbO_2}\varepsilon_{HbO_2\lambda_1} + C_{Hb}\varepsilon_{Hb\lambda_1}] \quad (5)$$

where $C_{HbO_2}$, $C_{Hb}$, are the concentration of oxyhemoglobin, and deoxyhemoglobin in the tissue sample, and $\varepsilon_{HbO_2\lambda_1}$, $\varepsilon_{Hb\lambda_1}$ are the extinction coefficients at the selected wavelength of the oxyhemoglobin and deoxyhemoglobin acquired using previously published data [43]. For multiple wavelengths, and by incorporating equation (1), the above proportionality can be represented as a matrix multiplication as shown in equation (6). Although only two wavelengths are shown in equation (6), it will be appreciated that any number of wavelengths may be used.

$$\Gamma\begin{bmatrix} \phi_{\lambda_1}\varepsilon_{HbO_2\lambda_1} & \phi_{\lambda_1}\varepsilon_{Hb\lambda_1} \\ \phi_{\lambda_2}\varepsilon_{HbO_2\lambda_2} & \phi_{\lambda_2}\varepsilon_{Hb\lambda_2} \end{bmatrix}\begin{bmatrix} C_{HbO_2} \\ C_{Hb} \end{bmatrix} \propto \begin{bmatrix} p_{\lambda_1} \\ p_{\lambda_2} \end{bmatrix} \quad (6)$$

Equation (6) takes the form of Ax=b, where A is the product of the Grüneisen parameter with the fluence and the extinction coefficient, x is the concentration of the chromophores in the tissue sample (x includes the unknown parameters in the matrix which need to be solved), and b is the pressure matrix. By implementing fluence matching, in accordance with the teachings herein, equation (6) can be re-written as equation (7).

$$\phi_{\lambda_3}\Gamma\begin{bmatrix} \varepsilon_{HbO_2\lambda_1} & \varepsilon_{Hb\lambda_1} \\ \varepsilon_{HbO_2\lambda_2} & \varepsilon_{Hb\lambda_2} \end{bmatrix}\begin{bmatrix} C_{HbO_2} \\ C_{Hb} \end{bmatrix} \propto \begin{bmatrix} p_{\lambda_1} \\ p_{\lambda_2} \end{bmatrix} \quad (7)$$

Restricting the solution in equation (7) can result in a more accurate prediction of the chromophore concentrations. For example, the solution to the chromophore concentrations is limited to positive values to avoid unreasonable results (e.g. to avoid negative concentrations) and the sum of all the chromophores at a selected location can be defined to add to 1. These two restrictions can be represented by $0 < C_{HbO_2}, C_{Hb} < 1$ and $C_{HbO_2} + C_{Hb} = 1$. The mean square error of the measured and calculated pressure may be minimized to solve for the chromophores concentrations.

In an alternative embodiment, depending on the hardware and software implementation, the fluence compensation method may be performed in real time or semi-real time (e.g. a few seconds) such that video playback of fluence compensated PA images and sO2 maps can be generated.

It should be noted that in some embodiments, downsampling may be performed on the RF acoustic response signals in order to generate PA images that have a smaller number of pixels both in cases where fluence compensation is performed and not performed.

Figure 5:
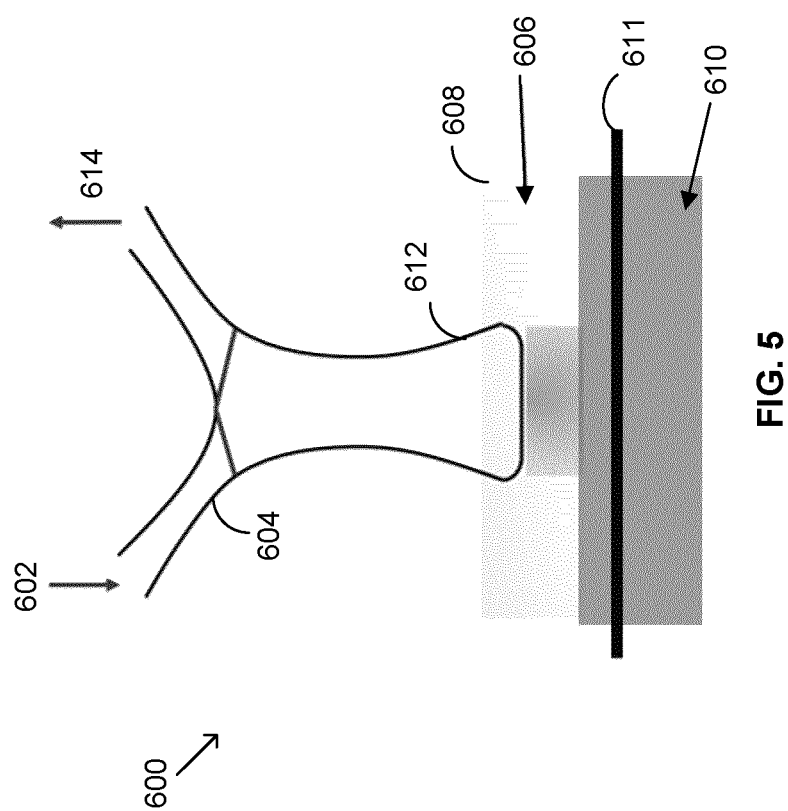
FIG. 5 is an illustrative view of a portion of the PA imaging system during testing with a tissue vessel phantom.

Referring now to FIG. 5, shown therein is an illustrative schematic view of a portion of the PA imaging system 600 during testing. The PA imaging system 600 can be calibrated and tested using a phantom 610 that is placed in a medium 606 in a container 608. The phantom 610 includes a tube 611 that is inserted into an upper portion of the phantom 610 just below the medium 606. The tube 611 may be used to hold a liquid, such as but not limited to blood, for imaging. The medium 606 may be degassed water or a liquid gel, such as an ultrasound gel. During actual use of the PA imaging system 600, the phantom 610 can be replaced with the actual sample. The sample may be an in vivo object, such as a mouse.

The PA imaging system 600 may include a heating lamp (not shown) for maintaining the phantom 610 (or sample during use) at certain temperature, such as a physiological temperature of 37±0.5° C. For example, the heating lamp may operate at 100 mW. The PA imaging system 600 may also include sensors (not shown) for monitoring various properties of the phantom 610 (or sample during use), such as a heating platform for monitoring temperature and/or electrocardiography leads for monitoring respiratory and heart rates.

In some embodiments, the PA imaging system 600 was a commercial PA system from FujiFilm-Visualsonics (Toronto, ON) called the vevoLAZR which has an electromagnetic stimulator (in this case a laser which is not shown) that provides a stimulus light signal 602 to an optical fiber bundle at 604 which directs the light signal 602 to illuminate the phantom 610. The laser may be an NIR ND: YAG Laser, operable at wavelengths of 680-970 nm. A transducer 612, comprising an array of ultrasound sensors, is operable to sense RF acoustic response signals that are generated by the phantom 610 (or sample during use) when it receives the stimulus light signal 602. For example, the transducer 612 can be a LZ-250 PA transducer with a center frequency of 21 MHz. Data 614 representing the measured acoustic response signals are stored and processed using fluence compensation in accordance with the teachings herein.

The PA imaging system 600 was tested using a phantom 610 composed of porcine tissue that was acquired from a local grocery store. A plastic tube 611 of 350 μm in diameter was inserted into pork tissue at approximately 5 mm below the tissue surface. Three different blood samples were prepared in EDTA coated vacutainers (Fisher Scientific, Hampton, USA). The blood was acquired from female CD1 mice using cardiac puncture. A first sample was prepared by gently mixing the vial to increase the oxygenation of the blood. A second sample was prepared by adding 1 mg of Sodium Nitrite (Sigma-Aldrich Inc., Canada) to 1 mL of blood to decrease its oxygenation. A third sample was prepared by mixing the first two samples. All three samples were then injected into the respective plastic tube separately. The porcine tissue with the tubes having the three blood samples were positioned as shown in FIG. 5 and then imaged. The oxygenation of the blood in each vial (i.e. tube) was also measured prior to imaging using a blood gas analyzer (Radiometer Medical, London, CA).

Figure 6:
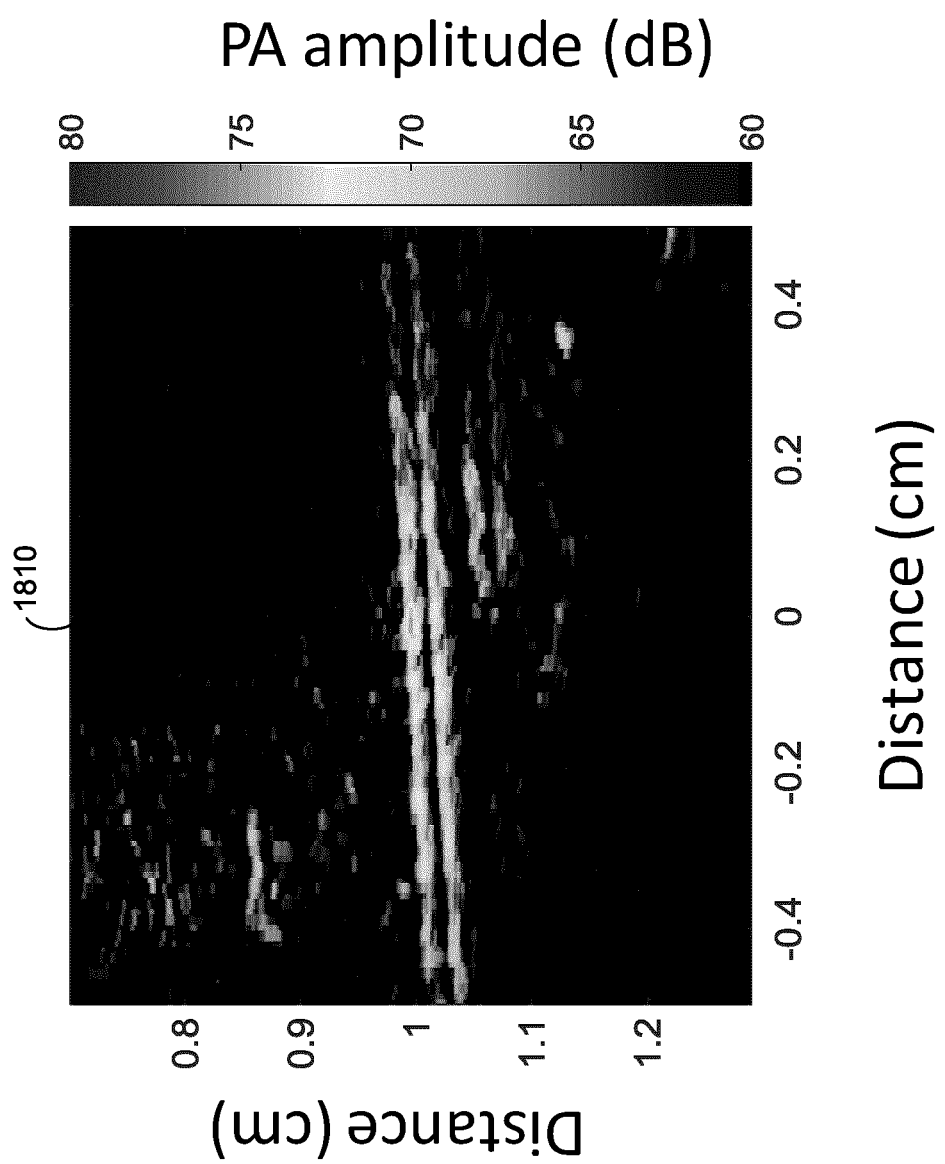
FIG. 6 shows an example of a PA image captured of the tissue vessel phantom.
Figure 7:
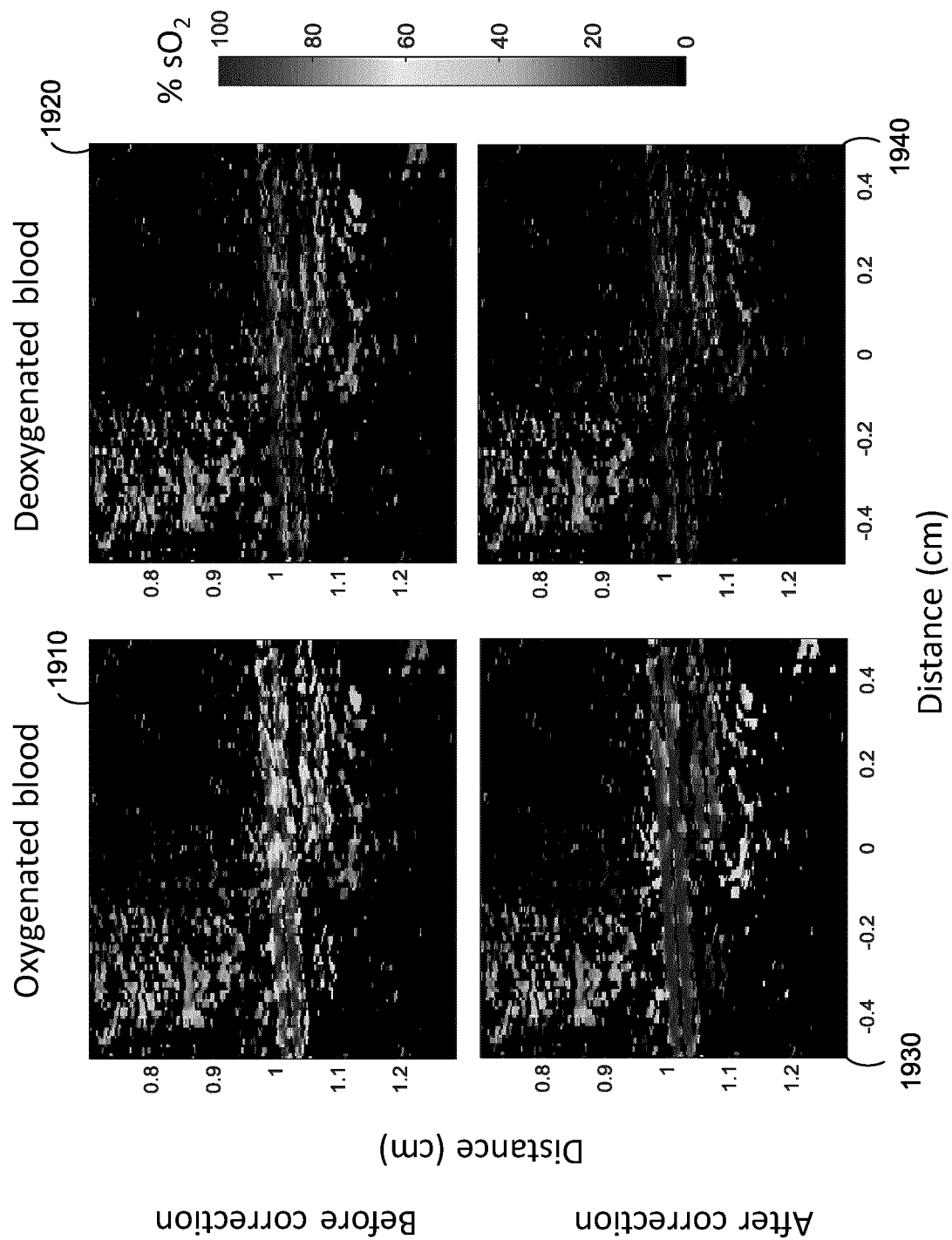
FIG. 7 shows an example of $sO_2$ maps before and after fluence correction for oxygenated blood and deoxygenated blood, respectively, in the tissue vessel phantom.

FIGS. 6-7 show example data that was obtained when the porcine tissue samples were imaged using separate light stimulus signals having optical wavelengths of 720 nm and 870 nm, respectively. Example PA image 1810 acquired at 720 nm is shown in FIG. 6. The fluence compensation techniques described herein were performed on uncompensated RF acoustic response signals obtained at 720 nm (i.e. the non-reference wavelength) which were fluence matched to reference RF acoustic response signals obtained at 870 nm (i.e. the reference wavelength). This creates compensated PA images for light stimuli at 720 nm that have the same fluence profiles as the reference PA image for the light stimuli at 870 nm. The compensated and reference PA images were used for linear spectral unmixing.

Example $sO_2$ maps 1910, 1920, 1930, and 1940 of the porcine tissue sample, generated by linear spectral unmixing are shown in FIG. 7. The $sO_2$ maps 1910 and 1930 show porcine tissue with oxygenated blood, whereas $sO_2$ maps 1920 and 1940 show porcine tissue with deoxygenated blood. The $sO_2$ maps 1930 and 1940 were processed using the fluence compensation techniques described herein, whereas $SO_2$ maps 1910 and 1920 were not.

The fluence uncompensated $sO_2$ map of porcine tissue with oxygenated blood 1910 shows a lower $sO_2$ estimate than that measured by the blood gas analyzer. Similarly, the fluence uncompensated $sO_2$ map of porcine tissue with deoxygenated blood 1920 shows a higher $sO_2$ estimate than that measured by the blood gas analyzer. This discrepancy is due to the effect of spectral coloring of tissue with depth [8]. The fluence compensated $sO_2$ maps 1930 and 1940 show a closer $sO_2$ to that measured by the blood glass analyzer. Table 1 shows these $sO_2$ measurements.

TABLE 1

Average $SO_2$ Measurements for Porcine Sample With and Without Fluence Compensation

|  | Oxygenated blood (expected 99%) | Mixed blood (expected 68%) | Deoxygenated blood (expected 1%) |
|---|---|---|---|
| Average $sO_2$ using uncorrected oxygenation estimate (%) | 80.91 ± 15.15 | 56.62 ± 20.44 | 13.04 ± 12.50 |
| Average $sO_2$ fluence matched oxygenation estimates (%) | 94.32 ± 8.24 | 64.50 ± 18.67 | 7.53 ± 10.80 |

Without fluence compensation, the difference between the estimate from the maps and the estimate from the blood gas analyzer were 18.3%, 16.7% and 12.2% for oxygenated, mixed and deoxygenated blood samples, respectively. With fluence compensation this difference decreased to 4.7%, 5.1% and 6.6%, respectively. Accordingly, the fluence compensation techniques described herein may improve the estimated $sO_2$ with depth.

Figure 8:
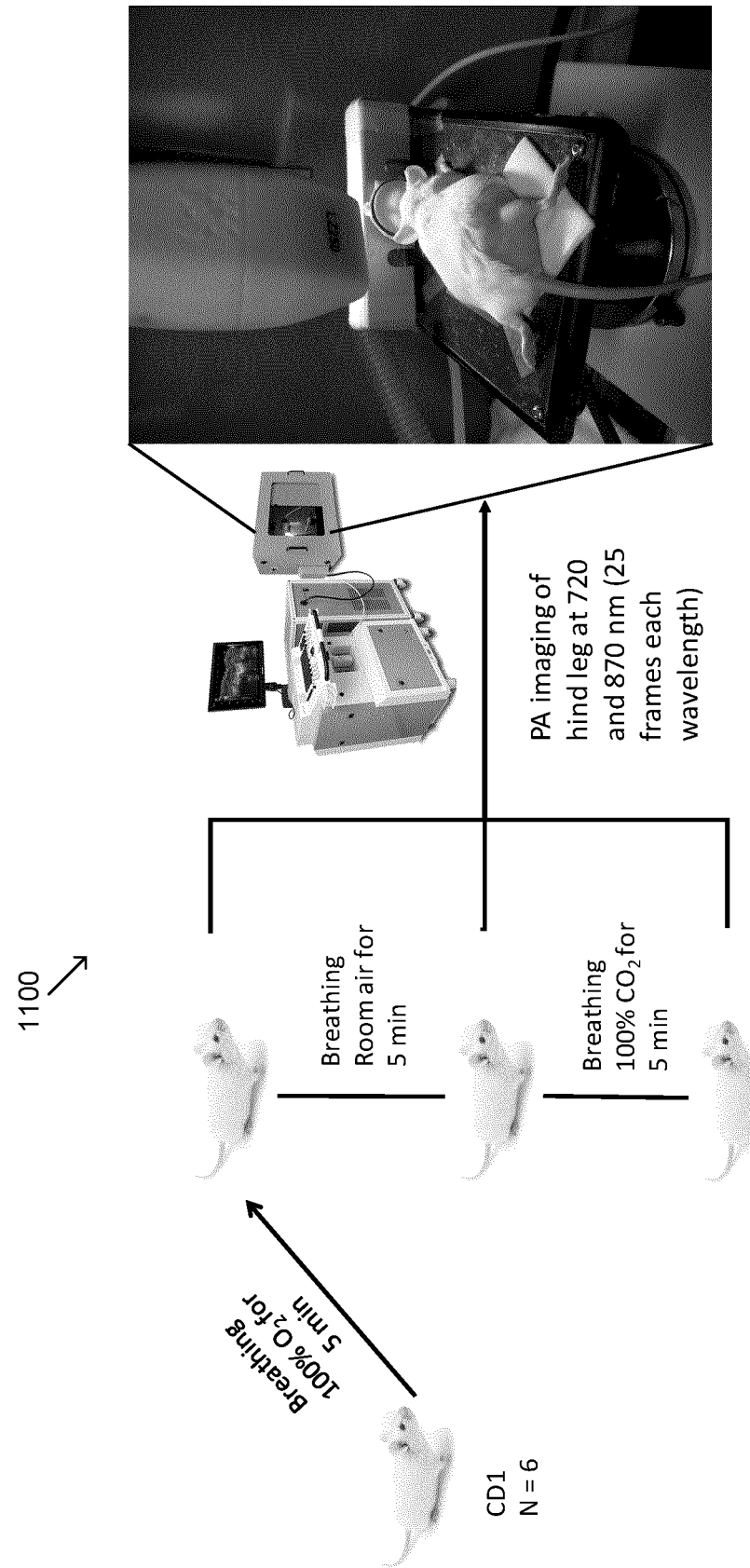
FIG. 8 shows an illustrative view of an example experimental setup for performing PA imaging using a mouse.
Figure 11A:
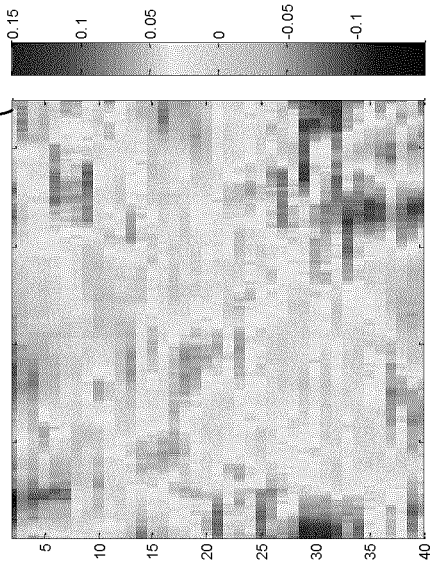
FIGS. 11A-11D shows an example of two SS maps and two cumulative SS maps for $O_2$ and $CO_2$, respectively.
Figure 11B:
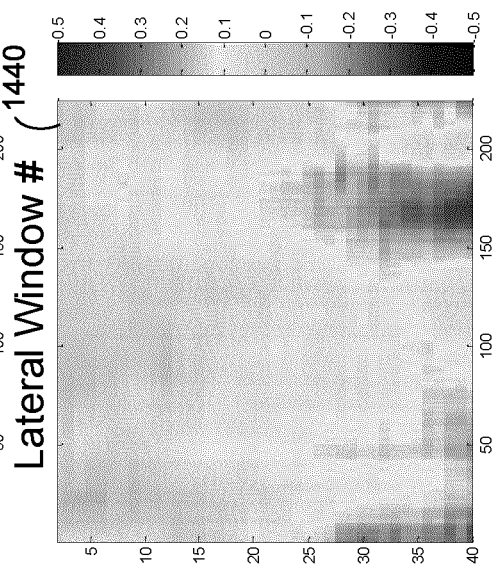
Figure 11C:
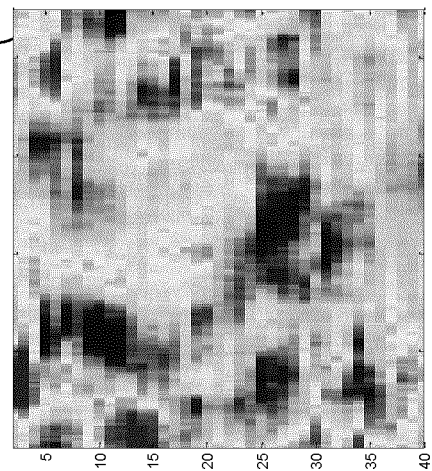
Figure 11D:
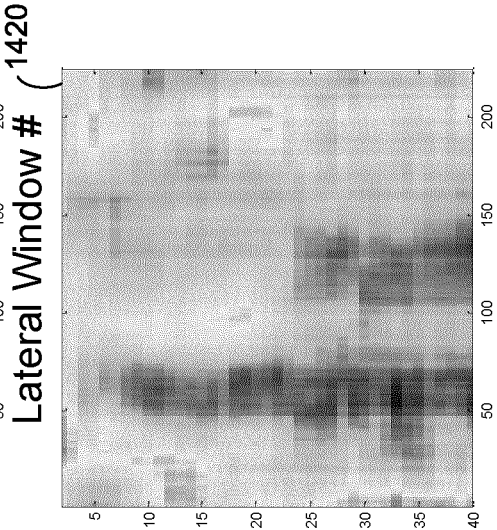

Further testing was performed using 6 female CD1 mice (Charles River, Toronto, CA) aged 7-8 weeks and weighing 25-30 g. The hair on the hind leg of each of the mice was removed using hair removal products prior to imaging. The mice were anaesthetized with a flow of isofluorane (1.5%) in air at 0.5-1 L/min. The breathing air was altered for each mouse starting with 100% 02 before switching to room air and terminating with 100% $CO_2$ inducing asphyxiation. Each of the 6 mice was imaged in each breathing condition, 100% 02, room air, and 100% $CO_2$. A period of 5 min was allowed for each breathing condition to ensure stabilization prior to imaging. FIG. 8 shows an illustrative view of an experimental setup 1100 for performing PA imaging with fluence compensation on the CD1 mice. All of the experimental protocols in this study were approved from the Animal Care Committee at St. Michaels Hospital and the Research Ethic Board at Ryerson University (protocol #788).

FIGS. 9A-14B show example data that was obtained when the sample mice were imaged using separate light stimulus signals having optical wavelengths of 720 nm and 870 nm, respectively. The fluence compensation techniques described herein were performed on uncompensated RF acoustic response signals obtained at 720 nm (i.e. the non-reference wavelength) to fluence match them to reference RF acoustic response signals obtained at 870 nm (i.e. the reference wavelength). This creates compensated PA images for light stimuli at 720 nm that have the same fluence profiles as the reference PA image for the light stimuli at 870 nm. The compensated and reference PA images were used for linear spectral unmixing.

PA images 1210 and 1220 for one mouse under one breathing condition are shown in FIGS. 9A and 9D for wavelengths at 720 and 870 nm, respectively. The PA images 1210 and 1220 were thresholded using the Otsu method in accordance with the techniques described herein. Although only 5 frames are shown for each of the PA images 1210 and 1220 in FIGS. 9B and 9E, respectively, for illustrative purposes, it will be appreciated that 25 frames were collected for each wavelength (at a frame rate of 5 frames/second). The RF acoustic response signals for PA images 1210 and 1220 were processed using the fluence compensation techniques described herein which involved determining the spectral slope for each spatial window for each segment of the RF acoustic response signals for PA image 1210 with respect to the RF acoustic response signals for PA image 1220. Accordingly, the RF acoustic response signals for the PA image 1220 obtained at a wavelength of 870 nm were defined as being the reference RF acoustic response signals.

Example spatial windows are shown at 1280 and 1290. Uncompensated power spectra 1230 and reference power spectra 1240 correspond to spatial windows 1280 and 1290. Uncompensated power spectra 1230 and reference power spectra 1240 were generated by normalizing and transforming into the frequency domain uncompensated and reference signal segments (not shown), respectively, using corresponding spatial windows, in accordance with the techniques described herein.

Uncompensated power spectra 1230 and reference power spectra 1240 were averaged to generate averaged uncompensated power spectrum 1250 and averaged reference power spectrum 1260, shown in FIGS. 9C and 9F, respectively, as well as in FIG. 10A.

FIG. 10B shows a power spectrum ratio 1312 between averaged uncompensated power spectrum 1250 and averaged reference power spectrum 1260. FIG. 10B also shows a line of best fit 1314 along a portion of the power spectrum ratio 1312 that corresponds to the bandwidth of the transducer in a logarithmic scale. The line of best fit 1314 was used to estimate the SS in accordance with the techniques disclosed herein.

Example maps of SS and cumulative SS are shown in FIGS. 11A-11D. The SS and cumulative SS maps 1410 and 1420 correspond to a mouse breathing 100% $O_2$, whereas the SS and cumulative SS maps 1430 and 1440 correspond a mouse breathing 100% $CO_2$. The SS and cumulative SS maps 1410 and 1420 show that negative SS and cumulative SS values are more common for the mouse breathing 100%

$O_2$, opposite to that of SS and cumulative SS maps 1430 and 1440, which show that positive SS and cumulative SS values are more common for the mouse breathing 100% $CO_2$. A higher magnitude of the cumulative SS indicates a higher correction for PA signal amplitude and oxygenation with depth. The cumulative SS may be used to create a frequency filter to provide fluence compensation in accordance with the techniques described herein.

Figure 12:
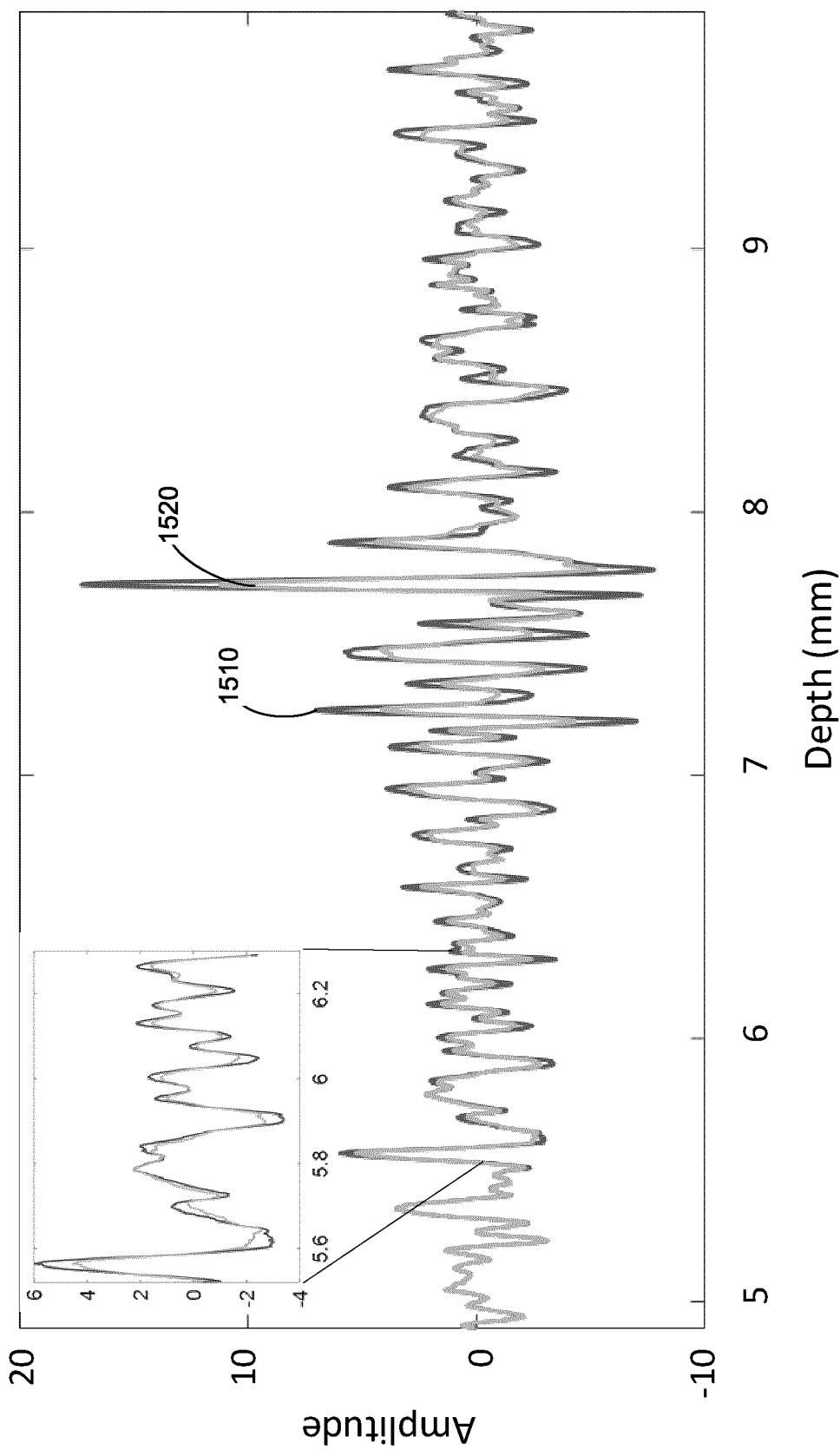
FIG. 12 shows an example of an RF acoustic response signal before and after fluence compensation.

FIG. 12 shows an example result of applying fluence compensation to an RF acoustic response signal for a PA image of a mouse breathing 100% O2. Uncompensated RF acoustic response signal 1510 is an example RF acoustic response signal before fluence compensation. Compensated RF acoustic response signal 1520 corresponds to uncompensated signal 1510 after undergoing fluence compensation. The amplitude of compensated RF acoustic response signal 1520 changes with depth in comparison to the uncompensated RF acoustic response signal 1510. The rate of change of the amplitude of the compensated RF acoustic response signal 1520 increases with depth in comparison to the uncompensated RF acoustic response signal 1510. A larger change in the amplitude of the compensated RF acoustic signal 1520 relative to the uncompensated RF acoustic response signal 1510 corresponds to a higher cumulative SS value.

Figure 13:
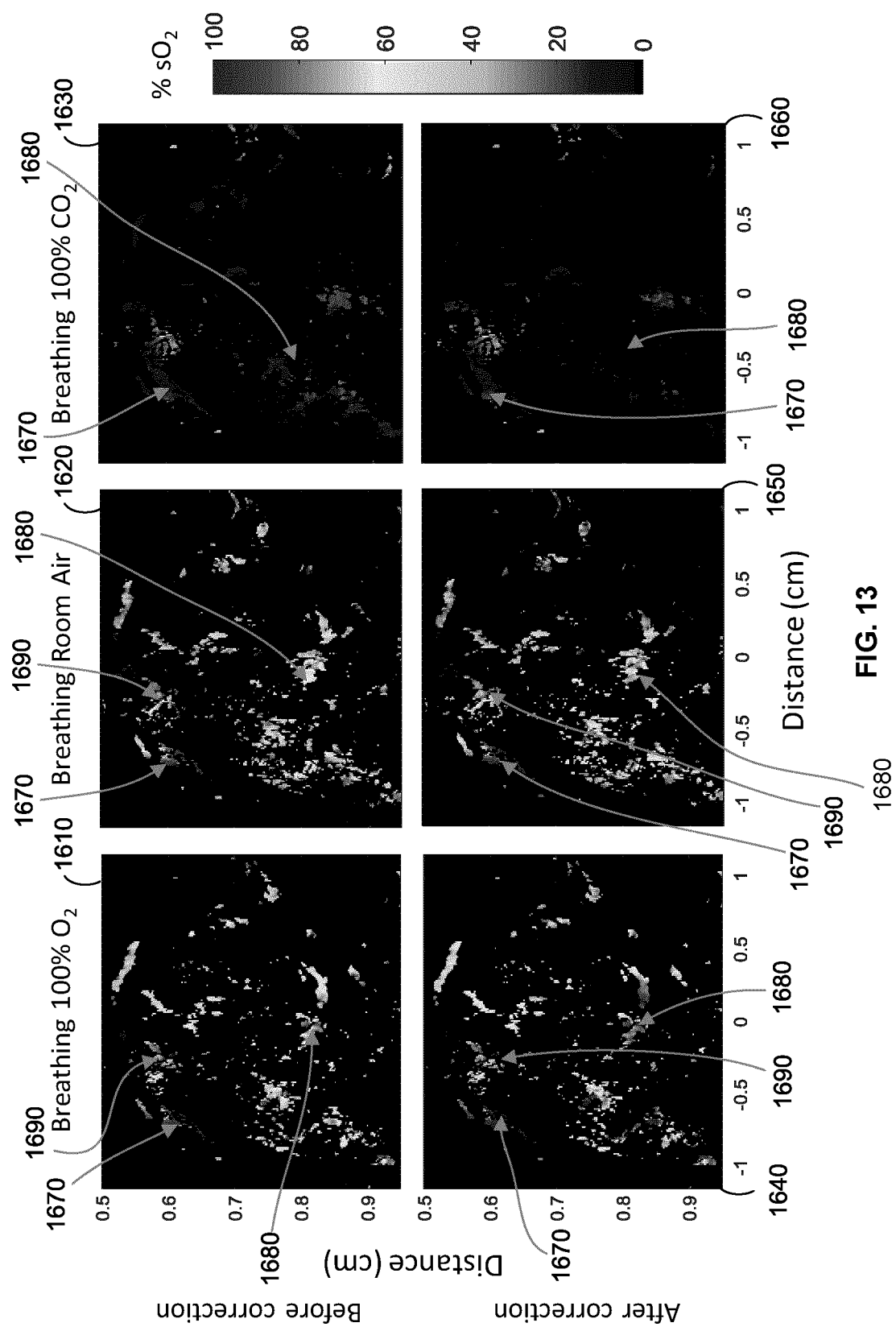
FIG. 13 shows an example of $sO_2$ maps before and after fluence correction.

FIG. 13 shows example $sO_2$ maps 1610, 1620, 1630, 1640, 1650, and 1660, which are generated by applying linear spectral unmixing on the PA images. The $sO_2$ maps 1610, 1620, 1630 correspond to PA images before fluence compensation. The $sO_2$ maps 1640, 1650, 1660 correspond to PA images after fluence compensation. The $sO_2$ maps 1610 and 1640 correspond to PA images of mice breathing 100% $O_2$. The $sO_2$ maps 1620 and 1650 correspond to PA images of mice breathing room air. The $sO_2$ maps 1630 and 1660 correspond to PA images of mice breathing 100% $CO_2$.

For superficial vessels 1670, the estimated $sO_2$ is similar before and after fluence compensation for the three breathing states. However, for deeper vessels 1680, the difference in the estimated $sO_2$ before and after fluence compensation is more pronounced. For the mice breathing 100% $O_2$, the estimated $SO_2$ became higher after correction. For the mice breathing 100% CO2, the estimated $SO_2$ became lower after correction. This result was expected because of the effect of spectral coloring is inverted for normoxic and hypoxic mice. Specifically, the optical absorption coefficient for oxygenated blood is higher at 870 nm than 720 nm, while for deoxygenated blood the trend is reversed. For mice breathing room air, the trend is more similar for the mice breathing 100% O2, albeit the correction is smaller.

Regions of Interest (ROIs) were applied to select multiple vessels at different depths in the $sO_2$ maps 1610, 1620, 1630, 1640, 1650, and 1660. The average $sO_2$ was computed for each ROI. FIG. 14A shows the difference in the estimated 502 between compensated $sO_2$ map 1640 and uncompensated $sO_2$ map 1610 (corresponding to a mouse breathing 100% $O_2$), as a function of depth from the skin. Each data point 1710 represents one selected vessel ROI. FIG. 14A also includes line of best fit 1720 to demonstrate the trend between the correction in $sO_2$ and the depth from skin.

Figure 14B:
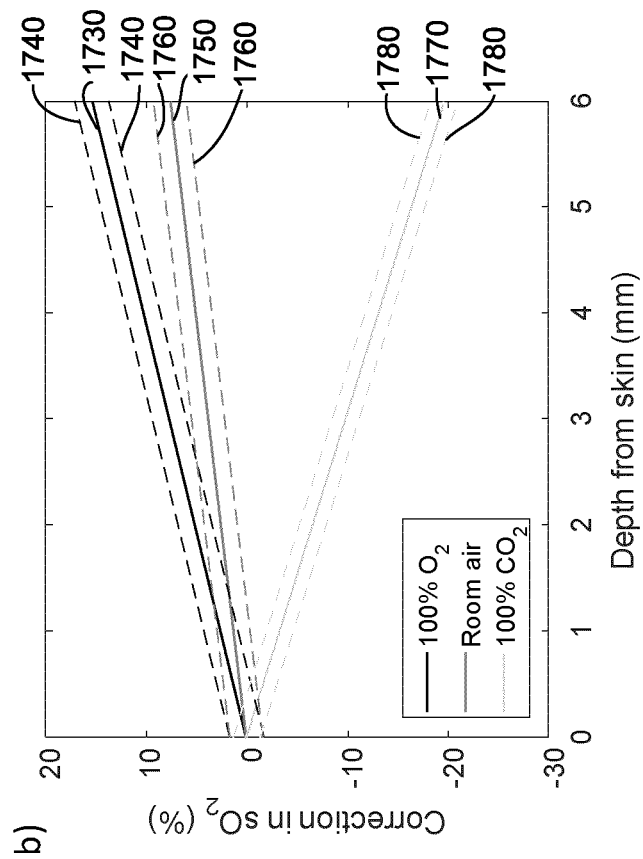
FIGS. 14A and 14B show an example of $sO_2$ correction as a function of depth.
Figure 14A:
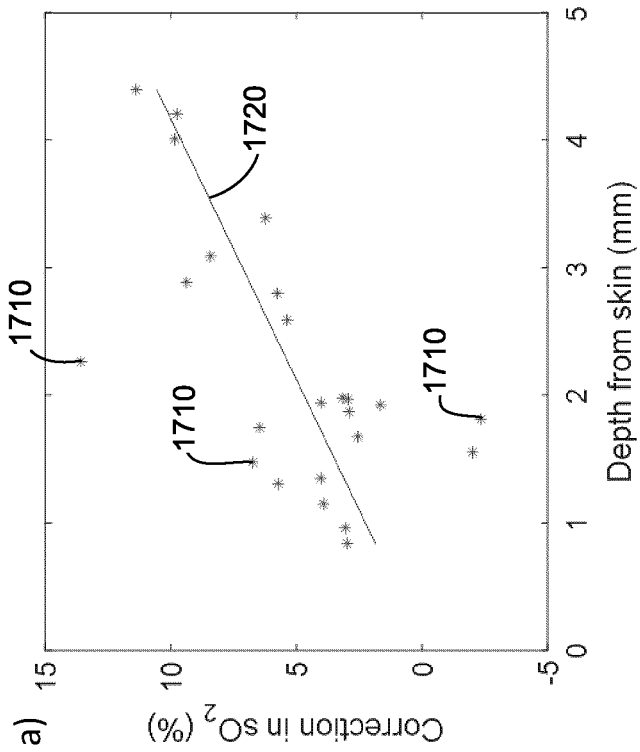

FIG. 14B shows the average line of best fit and standard deviation for the correction of $sO_2$ as a function of skin depth for each of the breathing states. The line of best fit 1730 and the standard deviation 1740 correspond to the mice breathing 100% $O_2$. The line of best fit 1750 and the standard deviation 1760 correspond to the mice breathing room air. The line of best fit 1770 and the standard deviation 1780 correspond to the mice breathing 100% $CO_2$.

The line of best fit 1730 for the mice breathing 100% $O_2$ shows a positive increase of $sO_2$ correction with depth of 2.67%/mm. The line of best fit 1750 of the mice breathing room air shows a positive increase of $sO_2$ correction with depth of 1.33%/mm. Accordingly, the fluence correction for the mice breathing 100% $O_2$ was higher than that for the mice breathing room air. For less oxygenated blood, the ratio of absorption coefficients at 870-720 nm decreases [8, 14]. Since room air only contains an average of 21% $O_2$, this result was expected.

The line of best fit 1770 for the mice breathing 100% $CO_2$ shows a negative increase of $SO_2$ correction with depth of 3.33%/mm. Accordingly, the fluence correction for the mice breathing 100% $CO_2$ is opposite that of the mice breathing 100% $O_2$ and room air. Since the absorption coefficient at 870-720 nm for deoxygenated blood is opposite that of oxygenated blood, this result was expected. Additionally, the amplitude of fluence correction for the mice breathing 100% $CO_2$ was higher than that of the mice breathing 100% $O_2$. For mice breathing 100% $O_2$, not all oxygenated vessels may be present due to consumption of oxygen by tissue, such as, for example, vessels 1690 shown in FIG. 13. However, for mice breathing 100% $CO_2$, all vessels may be deoxygenated.

These tests results show that extracting information from the PA RF spectral slope can be used to improve chromophore quantification for better oxygenation estimates. The spectral slope has been shown to carry information related to the PA absorbers' size and the light distribution. In multi-wavelength PA imaging, the absorbers' size remains unchanged and this allows the direct association between the spectral slope and the light distribution. A fluence compensation method that was developed using these insights results and tested as shown herein demonstrates a reduction in the influence of light distribution on the measured oxygenation values when testing was performed using mice.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

[1] L. Wang, K. Maslov, and L. V. Wang, "Single-cell label-free photoacoustic flowoxigraphy in vivo," Proc. Natl. Acad. Sci. U.S.A., vol. 110, no. 15, pp. 5759-5764, 2013.

[2] M. Sivaramakrishnan, K. Maslov, H. F. Zhang, G. Stoica, and L. V. Wang, "Limitations of quantitative photoacoustic measurements of blood oxygenation in small vessels," Phys. Med. Biol., vol. 52, no. 5, pp. 1349-1361, March 2007.

[3] S. Manohar and D. Razansky, "Photoacoustics: a historical review," Adv. Opt. Photonics, vol. 8, no. 4, pp. 586-617, December 2016.

[4] R. J. Paproski, A. Heinmiller, K. Wachowicz, and R. J. Zemp, "Multi-wavelength photoacoustic imaging of inducible tyrosinase reporter gene expression in xenograft tumors," Sci. Rep., vol. 4, June 2014.

[5] H. F. Zhang, K. Maslov, and L. V. Wang, "Effects of wavelength-dependent fluence attenuation on the noninvasive photoacoustic imaging of hemoglobin oxygen saturation in subcutaneous vasculature in vivo," presented at the 9th Conference on Photons Plus Ultrasound: Imaging and Sensing 2008, 2008.

[6] J. P. May, E. Hysi, L. A. Wirtzfeld, E. Undzys, S.-D. $L_1$, and M. C. Kolios, "Photoacoustic Imaging of Cancer Treatment Response: Early Detection of Therapeutic Effect from Thermosensitive Liposomes," *PloS One*, vol. 11, no. 10, p. e0165345, 2016.

[7] R. Ma, A. Taruttis, V. Ntziachristos, and D. Razansky, "Multispectral optoacoustic tomography (MSOT) scanner for whole-body small animal imaging," *Opt. Express*, vol. 17, no. 24, pp. 21414-21426, November 2009.

[8] B. Cox, J. G. Laufer, S. R. Arridge, and P. C. Beard, "Quantitative spectroscopic photoacoustic imaging: a review," *J. Biomed. Opt.*, vol. 17, no. 6, p. 061202, June 2012.

[9] S. L. Jacques, "Optical properties of biological tissues: a review," *Phys. Med. Biol.*, vol. 58, no. 11, pp. R37-61, June 2013.

[10] S. L. Jacques and B. W. Pogue, "Tutorial on diffuse light transport," *J. Biomed. Opt.*, vol. 13, no. 4, p. 041302, August 2008.

[11] Z. Yuan, Q. Wang, and H. Jiang, "Reconstruction of optical absorption coefficient maps of heterogeneous media by photoacoustic tomography coupled with diffusion equation based regularized Newton method," *Opt. Express*, vol. 15, no. 26, pp. 18076-18081, December 2007.

[12] Z. Yuan and H. Jiang, "Quantitative photoacoustic tomography: Recovery of optical absorption coefficient maps of heterogeneous media," *Appl. Phys. Lett.*, vol. 88, no. 23, p. 231101, June 2006.

[13] S. Bu et al., "Model-based reconstruction integrated with fluence compensation for photoacoustic tomography," *IEEE Trans. Biomed. Eng.*, vol. 59, no. 5, pp. 1354-1363, May 2012.

[14] B. T. Cox, J. G. Laufer, and P. C. Beard, "The challenges for quantitative photoacoustic imaging," presented at the Progress in Biomedical Optics and Imaging—Proceedings of SPIE, 2009, vol. 7177.

[15] J. Laufer, B. Cox, E. Zhang, and P. Beard, "Quantitative determination of chromophore concentrations from 2D photoacoustic images using a nonlinear model-based inversion scheme," *Appl. Opt.*, vol. 49, no. 8, pp. 1219-1233, March 2010.

[16] J. Laufer, D. Delpy, C. Elwell, and P. Beard, "Quantitative spatially resolved measurement of tissue chromophore concentrations using photoacoustic spectroscopy: application to the measurement of blood oxygenation and haemoglobin concentration," *Phys. Med. Biol.*, vol. 52, no. 1, pp. 141-168, January 2007.

[17] B. T. Cox, S. R. Arridge, K. P. Köstli, and P. C. Beard, "Two-dimensional quantitative photoacoustic image reconstruction of absorption distributions in scattering media by use of a simple iterative method," *Appl. Opt.*, vol. 45, no. 8, pp. 1866-1875, March 2006.

[18] R. J. Zemp, "Quantitative photoacoustic tomography with multiple optical sources," *Appl. Opt.*, vol. 49, no. 18, pp. 3566-3572, June 2010.

[19] A. Pulkkinen, B. T. Cox, S. R. Arridge, H. Goh, J. P. Kaipio, and T. Tarvainen, "Direct Estimation of Optical Parameters from Photoacoustic Time Series in Quantitative Photoacoustic Tomography," *IEEE Trans. Med. Imaging*, vol. 35, no. 11, pp. 2497-2508, 2016.

[20] M. Fonseca et al., "Three-dimensional photoacoustic imaging and inversion for accurate quantification of chromophore distributions," 2017, vol. 10064, pp. 1006415-1006415-9.

[21] M. A. Naser et al., "Improved photoacoustic-based oxygen saturation estimation with SNR-regularized local fluence correction," *IEEE Trans. Med. Imaging*, pp. 1-1, 2018.

[22] F. M. Brochu, J. Brunker, J. Joseph, M. R. Tomaszewski, S. Morscher, and S. E. Bohndiek, "Towards Quantitative Evaluation of Tissue Absorption Coefficients Using Light Fluence Correction in Optoacoustic Tomography," *IEEE Trans. Med. Imaging*, vol. 36, no. 1, pp. 322-331, January 2017.

[23] S. Tzoumas et al., "Eigenspectra optoacoustic tomography achieves quantitative blood oxygenation imaging deep in tissues," *Nat. Commun.*, vol. 7, p. ncomms12121, June 2016.

[24] T. Kirchner, J. Gröhl, and L. Maier-Hein, "Local context encoding enables machine learning-based quantitative photoacoustics," *ArXiv170603595 Phys.*, June 2017.

[25] J. R. Rajian, P. L. Carson, and X. Wang, "Quantitative photoacoustic measurement of tissue optical absorption spectrum aided by an optical contrast agent," *Opt. Express*, vol. 17, no. 6, pp. 4879-4889, March 2009.

[26] K. Daoudi, A. Hussain, E. Hondebrink, and W. Steenbergen, "Correcting photoacoustic signals for fluence variations using acousto-optic modulation," *Opt. Express*, vol. 20, no. 13, pp. 14117-14129, June 2012.

[27] P. Shao, T. J. Harrison, and R. J. Zemp, "Consecutively reconstructing absorption and scattering distributions in turbid media with multiple-illumination photoacoustic tomography," *J. Biomed. Opt.*, vol. 19, no. 12, p. 126009, December 2014.

[28] L. Yin, Q. Wang, Q. Zhang, and H. Jiang, "Tomographic imaging of absolute optical absorption coefficient in turbid media using combined photoacoustic and diffusing light measurements," *Opt. Lett.*, vol. 32, no. 17, pp. 2556-2558, September 2007.

[29] J. Ripoll and V. Ntziachristos, "Quantitative point source photoacoustic inversion formulas for scattering and absorbing media," *Phys. Rev. E Stat. Nonlin. Soft Matter Phys.*, vol. 71, no. 3 Pt 1, p. 031912, March 2005.

[30] S. Tzoumas, N. Deliolanis, S. Morscher, and V. Ntziachristos, "Unmixing Molecular Agents From Absorbing Tissue in Multispectral Optoacoustic Tomography," *IEEE Trans. Med. Imaging*, vol. 33, no. 1, pp. 48-60, January 2014.

[31] S. Tzoumas, A. Nunes, N. C. Deliolanis, and V. Ntziachristos, "Effects of multispectral excitation on the sensitivity of molecular optoacoustic imaging," *J. Biophotonics*, vol. 8, no. 8, pp. 629-637, August 2015.

[32] D. Razansky et al., "Multispectral opto-acoustic tomography of deep-seated fluorescent proteins in vivo," *Nat. Photonics*, vol. 3, no. 7, pp. 412-417, July 2009.

[33] J. Glatz, N. C. Deliolanis, A. Buehler, D. Razansky, and V. Ntziachristos, "Blind source unmixing in multi-spectral optoacoustic tomography," *Opt. Express*, vol. 19, no. 4, pp. 3175-3184, February 2011.

[34] S. Kim, Y.-S. Chen, G. P. Luke, and S. Y. Emelianov, "In vivo three-dimensional spectroscopic photoacoustic imaging for monitoring nanoparticle delivery," *Biomed. Opt. Express*, vol. 2, no. 9, pp. 2540-2550, August 2011.

[35] T. A. Bigelow, M. L. Oelze, and W. D. O'Brien, "Estimation of total attenuation and scatterer size from backscattered ultrasound waveforms," *J. Acoust. Soc. Am.*, vol. 117, no. 3 Pt 1, pp. 1431-1439, March 2005.

[36] T. A. Bigelow, B. L. McFarlin, W. D. O'Brien, and M. L. Oelze, "In vivo ultrasonic attenuation slope estimates for detecting cervical ripening in rats: Preliminary results," *J. Acoust. Soc. Am.*, vol. 123, no. 3, pp. 1794-1800, March 2008.

[37] G. J. Diebold, T. Sun, and M. I. Khan, "Photoacoustic monopole radiation in one, two, and three dimensions," *Phys. Rev. Lett.*, vol. 67, no. 24, pp. 3384-3387, December 1991.

[38] L. V. Wang, "Tutorial on Photoacoustic Microscopy and Computed Tomography," *IEEE J. Sel. Top. Quantum Electron.*, vol. 14, no. 1, pp. 171-179, 2008.

[39] M. Xu and L. V. Wang, "Photoacoustic imaging in biomedicine," *Rev. Sci. Instrum.*, vol. 77, no. 4, p. 041101, April 2006.

[40] G. Xu, I. A. Dar, C. Tao, X. Liu, C. X. Deng, and X. Wang, "Photoacoustic spectrum analysis for microstructure characterization in biological tissue: A feasibility study," *Appl. Phys. Lett.*, vol. 101, no. 22, p. 221102, November 2012.

[41] L. X. Yao, J. A. Zagzebski, and E. L. Madsen, "Backscatter coefficient measurements using a reference phantom to extract depth-dependent instrumentation factors," *Ultrason. Imaging*, vol. 12, no. 1, pp. 58-70, January 1990.

[42] X. Yang, X. Shen, J. Long, and H. Chen, "An Improved Median-based Otsu Image Thresholding Algorithm," *AASRI Procedia*, vol. 3, pp. 468-473, January 2012.

[43] N. Bosschaart, G. J. Edelman, M. C. G. Aalders, T. G. van Leeuwen, and D. J. Faber, "A literature review and novel theoretical approach on the optical properties of whole blood," *Lasers Med. Sci.*, vol. 29, no. 2, pp. 453-479, March 2014.

[44] E. Hysi, J. P. May, L. Writzfeld, E. Undyzs, S.-D. $L_1$, and M. C. Kolios, "Probing the in vivo changes in oxygen saturation with photoacoustic imaging as a non-invasive means of assessing treatment progression," presented at the Progress in Biomedical Optics and Imaging—Proceedings of SPIE, 2015, vol. 9323.

[45] S. Mallidi et al., "Multiwavelength Photoacoustic Imaging and Plasmon Resonance Coupling of Gold Nanoparticles for Selective Detection of Cancer," *Nano Lett.*, vol. 9, no. 8, pp. 2825-2831, August 2009.

The invention claimed is:

1. An imaging device for performing fluence compensation on a photoacoustic (PA) image of at least a portion of an object, the imaging device comprising:
   a preprocessing stage that is configured to:
      receive a set of reference RF acoustic response signals that were generated by the portion of the object when being illuminated with light having a reference wavelength, and a set of uncompensated RF acoustic response signals that were generated by the portion of the object when being illuminated with light having a non-reference wavelength, wherein the set of reference RF acoustic response signals and the set of uncompensated RF acoustic response signals are acquired using a transducer having a plurality of sensors at different sensor positions; and
      includes a beamformer for applying beamforming to generate preprocessed RF acoustic response signals comprising a set of preprocessed reference RF acoustic response signals and a set of preprocessed uncompensated RF acoustic response signals;
   a fluence compensation stage comprising:
      a segmentor to segment each signal of the set of preprocessed reference RF acoustic response signals and of the set of preprocessed uncompensated RF acoustic response signals into a set of reference segments and a set of uncompensated segments, respectively, using a set of overlapping spatial windows;
      a frequency transform block to perform a frequency transform on each of the sets of reference segments and each of the sets of uncompensated segments to generate corresponding sets of reference power spectra and corresponding sets of uncompensated power spectra, respectively;
      a filter stage that is configured to:
         generate filters that corresponds to each uncompensated segment of each preprocessed uncompensated RF acoustic response signal where a given filter is generated for a given uncompensated segment of a given preprocessed uncompensated RF acoustic response signal by averaging several uncompensated power spectra obtained at a common spatial window for other uncompensated RF acoustic response signals at adjacent sensor positions to a given sensor position used to acquire the given preprocessed uncompensated RF acoustic response signal to obtain an average uncompensated power spectrum, averaging several reference power spectra obtained at the common spatial window for corresponding reference RF acoustic response signals to obtain an average reference power spectrum and taking a ratio of the average uncompensated power spectrum to the average reference power spectrum; and
         filter each uncompensated segment of each preprocessed uncompensated RF acoustic response signal using the corresponding filter to generate compensated segments for each preprocessed uncompensated RF acoustic response signal; and
      a combiner to combine the compensated segments of each preprocessed uncompensated RF acoustic response signal to generate a set of fluence compensated RF acoustic response signals; and
   an image generator for generating the PA image of the portion of the object for the non-reference wavelength using the set of fluence compensated RF acoustic response signals.

2. The imaging device of claim 1, wherein the preprocessing stage further comprises a noise reduction stage for reducing noise in the reference and uncompensated RF acoustic response signals prior to the beamforming.

3. The imaging device of claim 1, wherein first and second halves of the uncompensated and reference power spectra used for averaging are the uncompensated and reference power spectra obtained for sensor positions to the left and right, respectively, of the given sensor position for which the average uncompensated and average reference power spectra is being determined.

4. The imaging device of claim 1, wherein the set of overlapping spatial windows are arranged along a depth direction for each signal of the set of preprocessed reference RF acoustic response signals and each signal of the set of preprocessed uncompensated RF acoustic response signals with an amount of overlapping between adjacent spatial windows defined by an overlap factor.

5. The imaging device of claim 1, wherein the filters are bandpass filters having a bandpass with a frequency range and amplitude values that are determined from the ratio of the average uncompensated power spectrum to the average reference power spectrum for the frequency range.

6. The imaging device of claim 5, wherein the ratio of the average uncompensated power spectrum to the average reference power spectrum in the frequency range is approximated using a line of best fit.

7. The imaging device of claim 5, wherein the frequency range corresponds to a response bandwidth of the transducer.

8. The imaging device of claim 1, wherein the imaging device further comprises a spectral decomposition stage that performs spectral decomposition using PA images that were generated from the set of reference RF acoustic response signals and one or more sets of compensated RF acoustic response signals that were fluence matched to the set of reference RF acoustic response signals to generate a spatial map of source generators that generated the set of reference RF acoustic response signals and the set of uncompensated RF acoustic response signals.

9. The imaging device of claim 8, wherein the spectral decomposition comprises linear spectral unmixing.

10. The imaging device of claim 8, wherein the object comprises a blood sample, and the spatial map of source generators comprises an oxygen saturation ($sO_2$) map.

11. The imaging device of claim 1, wherein the set of reference RF acoustic response signals and the set of uncompensated RF acoustic response signals are received from a data store or the set of reference RF acoustic response signals and the set of uncompensated RF acoustic response signals are received from the transducer.

12. The imaging device of claim 1, wherein the imaging device comprises at least one processor that is configured to operate as the preprocessing stage, the fluence compensation stage and the image generator.

13. A method for performing fluence compensation on a photoacoustic (PA) image of at least a portion of an object, the method comprising:
performing preprocessing by:
receiving a set of reference RF acoustic response signals that were generated by the portion of the object when being illuminated with light having a reference wavelength, and a set of uncompensated RF acoustic response signals that were generated by the portion of the object when being illuminated with light having a non-reference wavelength, wherein the set of reference RF acoustic response signals and the set of uncompensated RF acoustic response signals are acquired using a transducer having a plurality of sensors at different sensor positions; and
applying beamforming to generate preprocessed RF acoustic response signals comprising a set of preprocessed reference RF acoustic response signals and a set of preprocessed uncompensated RF acoustic response signals;
performing fluence compensation by:
segmenting each signal of the set of preprocessed reference RF acoustic response signals and of the set of preprocessed uncompensated RF acoustic response signals into a set of reference segments and a set of uncompensated segments, respectively, using a set of overlapping spatial windows;
performing a frequency transform on each of the sets of reference segments and each of the sets of uncompensated segments to generate corresponding sets of reference power spectra and corresponding sets of uncompensated power spectra, respectively;
generating filters that corresponds to each uncompensated segment of each preprocessed uncompensated RF acoustic response signal where a given filter is generated for a given uncompensated segment of a given preprocessed uncompensated RF acoustic response signal by averaging several uncompensated power spectra obtained at a common spatial window for other uncompensated RF acoustic response signals at adjacent sensor positions to a given sensor position used to acquire the given preprocessed uncompensated RF acoustic response signal to obtain an average uncompensated power spectrum, averaging several reference power spectra obtained at the common spatial window for corresponding reference RF acoustic response signals to obtain an average reference power spectrum and taking a ratio of the average uncompensated power spectrum to the average reference power spectrum; and
filtering each uncompensated segment of each preprocessed uncompensated RF acoustic response signal using the corresponding filter to generate compensated segments for each preprocessed uncompensated RF acoustic response signal;
combining the compensated segments of each preprocessed uncompensated RF acoustic response signal to generate a set of fluence compensated RF acoustic response signals; and
performing image generation by generating the PA image of the portion of the object for the non-reference wavelength using the set of fluence compensated RF acoustic response signals.

14. The method of claim 13, wherein the method further comprises reducing noise in the reference and uncompensated RF acoustic response signals prior to the beamforming.

15. The method of claim 13, wherein first and second halves of the uncompensated and reference power spectra used for averaging are the uncompensated and reference power spectra obtained for sensor positions to the left and right, respectively, of the given sensor position for which the average uncompensated and average reference power spectra is being determined.

16. The method of claim 13, wherein the set of overlapping spatial windows are arranged along a depth direction for each signal of the set of preprocessed reference RF acoustic response signals and each signal of the set of preprocessed uncompensated RF acoustic response signals with an amount of overlapping between adjacent spatial windows defined by an overlap factor.

17. The method of claim 13, wherein the filters are bandpass filters having a bandpass with a frequency range and amplitude values that are determined from the ratio of the average uncompensated power spectrum to the average reference power spectrum for the frequency range.

18. The method of claim 17, wherein the ratio of the average uncompensated power spectrum to the average reference power spectrum in the frequency range is approximated using a line of best fit.

19. The method of claim 17, wherein the frequency range corresponds to a response bandwidth of the transducer.

20. The method of claim 13, wherein the method further comprises performing spectral decomposition using PA images that were generated from the set of reference RF acoustic response signals and one or more sets of compensated RF acoustic response signals that were fluence matched to the set of reference RF acoustic response signals to generate a spatial map of source generators that generated the set of reference RF acoustic response signals and the set of uncompensated RF acoustic response signals.

21. The method of claim 20, wherein the spectral decomposition comprises linear spectral unmixing.

22. The method of claim 20, wherein the object comprises a blood sample, and the spatial map of source generators comprises an oxygen saturation ($sO_2$) map.

23. The method of claim 13, wherein the method further comprises performing at least one of displaying a fluence compensated PA image on a display and storing the fluence compensated PA image in a data store.

24. The method of claim 13, wherein the set of reference RF acoustic response signals and the set of uncompensated RF acoustic response signals are received from a data store or the set of reference RF acoustic response signals and the set of uncompensated RF acoustic response signals are received from the transducer.

25. The method of claim 13, wherein at least one processor is configured to provide the preprocessing, the fluence compensation and the image generation.

26. A computer-implemented method for performing fluence compensation on a photoacoustic (PA) image of at least a portion of an object, wherein the computer-implemented method comprises:

segmenting a set of preprocessed uncompensated RF acoustic response signals associated with a non-reference wavelength and a set of preprocessed reference RF acoustic response signals associated with a reference wavelength that is different than the non-reference wavelength into a set of uncompensated segments and a set of reference segments, respectively, using a set of overlapping spatial windows;

filtering each uncompensated segment of each preprocessed uncompensated RF acoustic response signal using corresponding filters to generate compensated segments for each preprocessed uncompensated RF acoustic response signal where a given corresponding filter has a bandpass that is defined using a power spectra ratio of a given uncompensated power spectra related to the uncompensated segment with respect to a given compensated power spectra related to the compensated segment that is at a common spatial window to the uncompensated segment;

combining the compensated segments of each preprocessed uncompensated RF acoustic response signal to generate a set of fluence compensated RF acoustic response signals; and generating the PA image of the portion of the object for the non-reference wavelength using the set of fluence compensated RF acoustic response signals.

27. The computer-implemented method of claim 26, wherein a transducer having a plurality of sensors at different sensor positions is used to obtain uncompensated RF acoustic response signals and reference RF acoustic response signals from which the set of preprocessed uncompensated RF acoustic response signals and the set of preprocessed reference RF acoustic response signals are derived and wherein the computer-implemented method further comprises determining the given uncompensated power spectra corresponding to a given sensor position by obtaining an average uncompensated power spectrum by averaging several uncompensated power spectra obtained at the common spatial window for other uncompensated RF acoustic response signals at adjacent sensor positions to the given sensor position and determining a given reference power spectrum by obtaining an average reference power spectrum at the common spatial window for corresponding reference RF acoustic response signals.

28. The computer-implemented method of claim 27, wherein the bandpass of the given corresponding filter amplitude values that are determined from a line of best fit of the given uncompensated power spectrum to the given reference power spectrum.

* * * * *